United States Patent
Maier et al.

(10) Patent No.: US 11,628,125 B2
(45) Date of Patent: Apr. 18, 2023

(54) PHOTOINITIATOR MODIFIED POLYACIDIC POLYMER

(71) Applicant: DENTSPLY SIRONA INC., York, PA (US)

(72) Inventors: Maximilian Maier, Osnabrück (DE); Joachim E. Klee, Radolfzell (DE); Christian Scheufler, Engen (DE); Caroline Renn, Singen (DE); Florian Szillat, Constance (DE)

(73) Assignee: DENTSPLY SIRONA INC., York, PA (US)

( * ) Notice: Subject to any disclaimer, the term of this patent is extended or adjusted under 35 U.S.C. 154(b) by 295 days.

(21) Appl. No.: 16/642,259

(22) PCT Filed: Aug. 30, 2018

(86) PCT No.: PCT/EP2018/073380
§ 371 (c)(1),
(2) Date: Feb. 26, 2020

(87) PCT Pub. No.: WO2019/043114
PCT Pub. Date: Mar. 7, 2019

(65) Prior Publication Data
US 2021/0069070 A1    Mar. 11, 2021

(30) Foreign Application Priority Data
Aug. 30, 2017 (EP) .................... 17188541
Oct. 18, 2017 (EP) .................... 17197057

(51) Int. Cl.
*A61K 6/889* (2020.01)
*A61K 6/62* (2020.01)
*C08F 8/32* (2006.01)
*C08F 220/64* (2006.01)

(52) U.S. Cl.
CPC ........... *A61K 6/889* (2020.01); *A61K 6/62* (2020.01); *C08F 8/32* (2013.01); *C08F 220/64* (2013.01)

(58) Field of Classification Search
CPC .................................................. A61K 6/889
See application file for complete search history.

(56) References Cited

U.S. PATENT DOCUMENTS

| | | | |
|---|---|---|---|
| 3,655,605 A | 4/1972 | Smith | |
| 3,814,717 A | 6/1974 | Wilson | |
| 4,143,018 A | 3/1979 | Crisp | |
| 4,209,434 A | 6/1980 | Crisp | |
| 4,298,738 A | 11/1981 | Lechtken | |
| 4,324,744 A | 4/1982 | Lechtken | |
| 4,360,605 A | 11/1982 | Schmitt | |
| 4,376,835 A | 3/1983 | Schmitt | |
| 4,385,109 A | 5/1983 | Lechtken | |
| 4,814,362 A | 3/1989 | Billington | |
| 5,154,762 A | 10/1992 | Mitra | |
| 5,318,929 A | 6/1994 | Jana | |
| 5,360,770 A | 11/1994 | Chadwick | |
| 5,501,727 A | 3/1996 | Wang | |
| 5,545,676 A | 8/1996 | Palazzotto | |
| 2004/0079258 A1 | 4/2004 | Hoescheler | |
| 2012/0046376 A1 | 2/2012 | Loccufier | |
| 2016/0160061 A1 | 6/2016 | Gaudl | |

FOREIGN PATENT DOCUMENTS

| | | | | |
|---|---|---|---|---|
| EP | 0173567 A2 | 3/1986 | | |
| KR | 20150000063 A | 1/2015 | | |
| WO | 9522956 A1 | 8/1995 | | |
| WO | 2016156363 A1 | 10/2016 | | |
| WO | WO-2016202744 A1 * | 12/2016 | ............ | C08F 226/02 |
| WO | 2017042333 A1 | 3/2017 | | |
| WO | 2017060459 A1 | 4/2017 | | |

OTHER PUBLICATIONS

Glass Ionomer Cement Formulations: I. The Preparation of Novel Fluoroaluminosilicate Glasses High in Fluorine; B. Kent et al; Journal of Dental Research; Jun. 1979; pp. 1607-1619; 58(6).
International Search Report; PCT/EP2018/073380; Nov. 14, 2018 (completed); dated Nov. 23, 2018.
International Preliminary Report on Patentability; PCT/EP2018/073380; Nov. 14, 2018 (completed); dated Nov. 23, 2018.
Written Opinion of the International Searching Authority; PCT/EP2018/073380; Nov. 14, 2018 (completed); dated Nov. 23, 2018.

* cited by examiner

*Primary Examiner* — Michael F Pepitone
(74) *Attorney, Agent, or Firm* — Dentsply Sirona Inc.

(57) ABSTRACT

The present invention relates to an initiator modified polyacidic polymer having a covalently bonded initiator compound, and to a dental resin-modified glass ionomer composition comprising this polyacidic polymer. Furthermore, the present invention relates to a use of the initiator modified polyacidic polymer for the preparation of a dental composition.
The covalently bonded initiator compound of the initiator modified polyacidic polymer may be any compound of a redox initiator system, a photoinitiator system, for example a Norrish type I or II photoinitiator, an electron donor component, a sensitizer component or a coinitiator component.

13 Claims, No Drawings

PHOTOINITIATOR MODIFIED POLYACIDIC POLYMER

CROSS-REFERENCE TO RELATED APPLICATIONS

This application is a national stage of PCT/EP20181073380, filed Aug. 30, 2018, which claims priority to European Patent Application No. 17188541.1, filed on Aug. 30, 2017 and European Patent Application No. 17197057.7, filed on Oct. 18, 2017, which are herein incorporated by reference for all purposes.

FIELD OF THE INVENTION

The present invention relates to a dental resin-modified glass ionomer composition comprising a specific initiator modified polyacidic polymer having a covalently bonded initiator compound. The present invention also relates to a specific initiator modified polyacidic polymer having a covalently bonded initiator compound. Furthermore, the present invention relates to a use of the initiator modified polyacidic polymer for the preparation of a dental composition.

The covalently bonded initiator compound of the initiator modified polyacidic polymer may be a Norrish type I initiator compound or a sensitizer or electron donor component of a Norrish type II initiator. Moreover, the covalently bonded initiator compound of the initiator modified polyacidic polymer may be a oxidizing compound or a reducing compound in of a redox initiator system.

BACKGROUND OF THE INVENTION

Dental compositions containing polymerizable components require an initiator system for curing. The initiator system may be a photoinitiator system which is activated by visible light in the range of from 400 to 800 nm. Alternatively or additionally, the initiator system may comprise a self-curing redox initiator system which is activated when different components of the redox initiator are mixed.

A resin-modified glass ionomer composition is a polymerizable component containing dental composition further comprising a reactive particulate glass and polyacidic polymer which is reactive with the reactive particulate filler in a cement reaction. Resin-modified glass ionomer compositions are cured by two independent curing mechanisms including a cement reaction and a radical polymerization. A cement reaction requires cations from the reactive particulate glass to leach into a hydrophilic surface layer of the particles before a salt forming reaction with the acidic groups of the polyacidic polymer may take place. On the other hand, a photopolymerization of polymerizable monomers takes place in the bulk of the composition. In order to efficiently initiate photopolymerization, polymerizable monomers and photoinitiator should be in close proximity.

Photoinitiator compounds for use in dental compositions are small molecules which may leach out of the cured composition, which may give rise to toxicological concerns.

Polyacidic polymers having a covalently bonded initiator compound are known. KR 2015/0000063 A discloses a photo-crosslinkable polyacrylic acid as a binder for a silicon-based anode for a lithium ion battery. In the photo-crosslinkable polyacrylic acid, a photoreactive residue is derived from a benzophenone compound such as 4-(6-hydroxyhexyloxy)benzophenone. Specifically, the photo-crosslinkable polyacrylic acid is prepared by reacting polyacrylic acid and 4-(6-hydroxyhexyloxy)benzophenone in the presence of the coupling agent 1-[3-(dimethylamino) propyl]-3-ethylcarbodiimide methiodide (EDC), with a degree of substitution with 4-(6-hexyloxy)benzophenone groups of about 3.7%. However, the photo-crosslinkable polyacrylic acid of KR 2015/0000063 A does not react in a cement reaction.

SUMMARY OF THE INVENTION

It is an object of the present invention to provide a dental resin-modified glass ionomer composition having
    improved color stability;
    improved biocompatibility; and
    excellent mechanical properties after curing, in particular in view of flexural strength.

Moreover, it is the problem of the present invention to provide a use of the initiator modified polyacidic polymer for the preparation of a dental composition.

According to a first aspect, the present invention provides a dental resin-modified glass ionomer composition comprising
  (a) a reactive particulate filler, and
  (b) a polyacidic polymer which is reactive with the reactive particulate filler in a cement reaction, wherein the composition further comprises,
  wherein at least one of the one or more initiator compounds is an aromatic amine which is linked to the polyacidic polymer (b) by a covalent bond forming an initiator modified polyacidic polymer having a covalently bonded aromatic amine initiator compound, wherein the initiator modified polyacidic polymer is a compound having repeating units of the following formula (I):

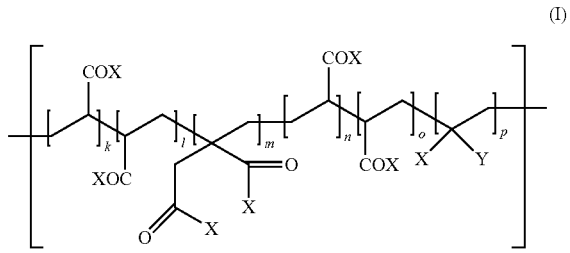

wherein
  X, which may be the same or different, independently represent OH, O—L—Z, or NH—L—Z, wherein
    L is a single bond or a divalent linker group, and
    Z is a covalently bonded initiator compound;
  Y is a hydrogen atom, COOH or a covalently bonded initiator compound;
  k, l, m, n, o and p are independently integers of at least 0, k+l+m+n+o+p is at least 1; and
  at least one X is present which is not OH when Y is a hydrogen atom or COOH;
  wherein the polyacidic polymer has a weight average molecular weight of 1 to 300 kDa;
  wherein the initiator modified polyacidic polymer contains 0.01 to 20 mole % covalently bonded initiator compound per 100 mole % of acidic groups of the polyacidic polymer.

According to a second aspect, the present invention provides an initiator modified polyacidic polymer having a covalently bonded aromatic amine initiator compound, wherein the initiator modified polyacidic polymer contains 0.01 to 20 mole % covalently bonded initiator compound per 100 mole % of acidic groups of the initiator modified polyacidic polymer, wherein the initiator modified polyacidic polymer is a compound having repeating units of the following formula (I):

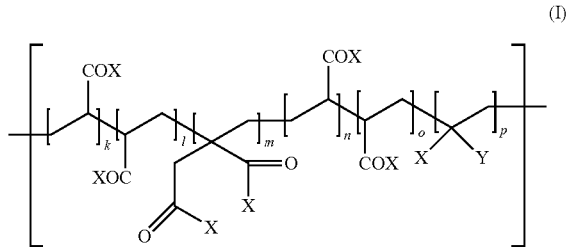

wherein
X, which may be the same or different, independently represent OH, O—L—Z, or NH—L—Z, wherein
L is a single bond or a divalent linker group, and
Z is a covalently bonded aromatic amine initiator compound;
Y is a hydrogen atom, COOH or a covalently bonded aromatic amine initiator compound;
k, , m, n, o and p are independently integers of at least 0, k+l+m+n+o+p is at least 1; and
at least one X is present which is not OH when Y is a hydrogen atom or COOH; and wherein the polyacidic polymer has a weight average molecular weight of 1 to 300 kDa.

According to a third aspect, the present invention provides a use of the polyacidic polymer according to the second aspect of the present invention for the preparation of a dental composition.

The present invention is based on the recognition that an initiator compound covalently attached to a polyacidic polymer may be used in a dental resin-modified glass ionomer composition for efficiently initiating a radical curing mechanism. Surprisingly, an initiator modified polyacidic polymer which is involved in a cement reaction on the hydrophilic surface of a particulate reactive glass may at the same time efficiently initiate an independent curing mechanism in the hydrophobic bulk of the dental composition.

Accordingly, it was found that an initiator modified polyacidic polymer having a covalently bonded initiator compound provides a cured dental resin-modified glass ionomer composition which has improved color stability, improved biocompatibility, and excellent mechanical properties after curing, in particular in view of flexural strength. Specifically, yellowing is significantly reduced compared to conventional dental resin-modified glass ionomer compositions having non-covalently bonded initiator compounds. In addition, the leaching problem of the cured dental resin-modified glass ionomer composition is alleviated.

DETAILED DESCRIPTION OF PREFERRED EMBODIMENTS

The term "resin-modified" as used herein means that a resin in the form of polymerizable monomers is contained in the dental glass ionomer composition.

The term "reactive particulate filler" refers to any particulate component capable of reacting with the polyacidic polymer (b) in a cement reaction. The term "cement reaction" means an acid-base reaction between the reactive particulate filler (a) and the polyacidic polymer (b). Specifically, the reactive particulate filler (a) is alkaline and reacts with the acid groups, such as carboxylic groups of the polyacidic polymer, whereby an acid-base reaction takes place resulting in the formation of ionic bonds.

The term "polyacidic" in connection with the polyacidic polymer means that the polymer has a plurality of acidic groups, preferably carboxylic acid groups, which may participate in a cement reaction with the reactive particulate filler (a). For example, the acidic groups in the form of carboxylic acid groups are preferably present in the backbone of the polymer and may be derived from (meth)acrylic acid, maleic acid and/or itaconic acid.

The term "initiator system" means any system of one or a mixture of two or more compounds that form free radicals when activated, e. g. by exposure to light and/or interaction with one or more further compounds in a photochemical or redox process, whereby polymerization of polymerizable compounds is initiated. The initiator system may be a photoinitiator system consisting of one or more initiator compounds generating alone or in combination free radicals when irradiated with light having a wavelength in the range of from 400 to 800 nm. Alternatively, the initiator system may be a redox initiator system consisting of two or more initiator compounds generating free radicals when mixed.

The term "initiator compound" in connection with the initiator system means any compound of the initiator system, for example a redox initiator component, a Norrish type I or II photoinitiator, an electron donor component, a sensitizer component or a coinitiator component. The term "photoinitiator" refers to any chemical compound that forms free radicals when activated, e. g. by exposure to light or interaction with a sensitizer in a photochemical process. The term "electron donor" refers to any compound which is capable of donating electrons in a photochemical process, for example organic compounds having heteroatoms with electron lone pairs, such as amine compounds. The term "sensitizer" refers to a molecule that produces a chemical change in another molecule such as the photoinitiator in a photochemical process. The term "coinitiator" refers to any compound improving the polymerization performance of the photoinitiator, for example Iodonium, sulfonium and phosphonium salts and tertiary aromatic phosphine compounds.

The term "initiator modified" in connection with the polyacidic polymer means that any initiator compound of the initiator system is linked to the polyacidic polymer by a covalent bond.

The present dental resin-modified glass ionomer composition provides a cured dental glass-ionomer composition based on a cement reaction of the reactive particulate filler (a) and the polyacidic polymer (b) in combination with a polymerization of a resin, which free radical polymerization is initiated by the initiator system.

The present invention relates to a dental resin-modified glass ionomer composition, which may be used as a temporary or final restoration of a hard dental tissue or as a luting cement for crowns and bridge cementations.

The Reactive Particulate Filler (a)

The dental resin-modified glass ionomer composition according to the present invention comprises (a) a reactive particulate filler. The dental resin-modified glass ionomer composition may comprise one or a mixture of two or more reactive particulate fillers (a).

Any granular component being reactive with the polyacidic polymer (b) in a cement reaction may be used as the reactive particulate filler (a), that is, any alkaline granular compound suitable for a dental resin-modified glass ionomer composition.

Preferably, the reactive particulate filler (a) is one or a mixture of two or more metal oxides, most preferably a glass, i.e. an amorphous solid mixture of metal oxides.

The reactive particulate filler (a) in the form of a glass is obtainable by transforming a solid mixture of metal oxides by a thermal melt process into a glass followed by milling, which glass is capable of reacting with the polyacidic polymer (b) in a cement reaction Any conventional reactive dental glass may be used as reactive particulate filler (a). Specific examples of particulate reactive glasses are selected from calcium alumina silicate glass, calcium alumina fluorosilicate glass, calcium aluminumfluoroborosilicate glass, strontium aluminosilicate glass, strontium aluminofluorosilicate glass, strontium aluminofluoroborosilicate glass, or ion-leachable glasses, e.g. as described in U.S. Pat. Nos. 3,655,605, 3,814,717, 4,143,018, 4,209,434, 4,360,605 and 4,376,835.

Alternatively or additionally, reactive metal oxides such as zinc oxide and/or magnesium oxide may be used in glass and/or crystalline form as reactive particulate filler (a).

Preferably, the reactive particulate filler (a) is a glass comprising:
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride.

The present dental resin-modified glass ionomer composition preferably comprises 20 to 90 percent by weight of the reactive particulate filler (a), more preferably 30 to 85 percent by weight, most preferably 20 to 80 percent by weight based on the total weight of the composition.

The reactive particulate filler (a) usually has an average particle size of from 0.1 to 100 μm, preferably of from 1 to 40 μm as measured, for example, by electron microscopy or by using a conventional laser diffraction particle sizing method as embodied by a MALVERN Mastersizer S or MALVERN Mastersizer 2000 apparatus.

The reactive particulate filler (a) may have a unimodal or multimodal (e.g., bimodal) particle size distribution, wherein a multimodal reactive particulate filler (a) represents a mixture of two or more particulate fractions having different average particle sizes.

The reactive particulate filler (a) may be an agglomerated reactive particulate filler which is obtainable by agglomerating a reactive particulate filler in the presence of a modified polyacid and/or polymerizable resin such as (meth) acryloyl monomers. The particle size of the agglomerated reactive particulate filler (a) may be adjusted by suitable size-reduction processes such as milling.

The reactive particulate filler (a) may be surface modified by a surface modifying agent. Preferably, the surface modifying agent is a silane. A silane provides a suitable hydrophobicity to the reactive particulate filler (a), which allows for an advantageous, homogeneous admixture with organic components of the dental resin-modified glass ionomer composition. The reactive particulate filler (a) may have silane coupling agent(s) on its surface, for example in the form of a coating at least partly, and preferably fully covering the surface of the reactive particulate filler (a).

The Polyacidic Polymer (b) and the Initiator System

The dental resin-modified glass ionomer composition according to the present invention comprises (b) a polyacidic polymer which is reactive with the reactive particulate filler in a cement reaction. The dental resin-modified glass ionomer composition may comprise one or a mixture of two or more polyacidic polymers (b).

The polyacidic polymer (b) is initiator modified, that is, it is formed by linking at least one or more initiator compounds to the polyacidic polymer (b) by a covalent bond. At least one initiator compound is an aromatic amine initiator compound.

Preferably, in the polyacidic polymer (b), the plurality of acidic groups comprises acidic groups selected from a group $(C=Het_1)-Het_2H$, wherein $Het_1$ is an oxygen atom or a sulfur atom, and $Het_2$ is an oxygen atom or a sulfur atom. That is, the acidic groups are preferably selected from carboxylic acid group $((C=O)-OH)$, $(C=S)-SH$, $(C=O)-SH$ and $(C=S)-OH$. The most preferred acidic group is the carboxylic acid group $((C=O)-OH)$.

The acidic groups of the polyacidic polymer (b) can react with the reactive particulate filler (a) to form a glass ionomer cement which can be used as a dental material.

Preferably, the polyacidic polymer (b) is water-soluble. The term "water-soluble" means that at least 0.1 g, preferably 0.5 g of the polyacidic polymer (b) dissolves in 100 g of water at 20° C.

Furthermore, it is preferred that the polyacidic polymer (b) is hydrolysis-stable. "Hydrolysis-stable" means that the polyacidic polymer (b) is stable to hydrolysis in an acidic medium, such as in a dental composition. Specifically, the polyacidic polymer (b) preferably does not contain groups such as ester groups which hydrolyze in aqueous media at pH 3 at room temperature within one month.

The polyacidic polymer (b) is an initiator modified polyacidic polymer having repeating units of the following formula (I):

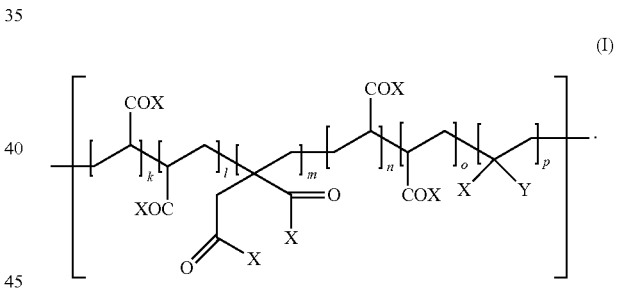

In formula (I), the X, which may be the same or different, independently represent OH, O—L—Z, or NH—L—Z, wherein L is a single bond or a divalent linker group, and Z is a covalently bonded initiator compound. Y is a hydrogen atom, COOH or a covalently bonded initiator compound, and k, l, m, n, o and p are independently integers of at least 0, wherein k+l+m+n+o+p is at least 1. In formula (I), at least one X is present which is not OH when Y is a hydrogen atom or COOH. At least one initiator compound is an aromatic amine initiator compound.

The initiator modified polyacidic polymer having repeating units of formula (I) has a weight average molecular weight of 1 to 300 kDa, preferably 10 to 250 kDa.

When the initiator modified polyacidic polymer having repeating units of the formula (I) has a weight-average molecular weight of less than 1 kDa, the strength of the cured dental resin-modified glass ionomer composition may be lowered. On the other hand, when the initiator modified polyacidic polymer having repeating units of the formula (I) has a weight-average molecular weight exceeding 300 kDa, upon mixing and blending the dental resin-modified glass ionomer composition may become too viscous, whereby workability may perhaps be deteriorated. Therefore, the weight-average molecular weight of the initiator modified polyacidic polymer having repeating units of the formula (I) is from 1 to 300 kDa.

In formula (I), the divalent linker group L of group X may be a hydrocarbon group which may be aliphatic and/or aromatic, preferably aliphatic, and preferably has 1 to 45 carbon atoms. The aliphatic hydrocarbon group may be saturated or unsaturated. The hydrocarbon group may be substituted with 1 to 6 $C_{1-4}$ alkyl groups. Specific examples of the alkyl groups are methyl, ethyl, n-propyl, i-propyl, n-butyl, i-butyl or tert.-butyl. In a preferred embodiment, for L, the hydrocarbon group of the linker group may contain 1 to 20 heteroatoms selected from oxygen, nitrogen and sulphur. The oxygen atoms, nitrogen atoms and sulphur atoms in the hydrocarbon group may be in the form of ether or thioether bonds, amine bonds, keto or sulfoxide groups, carboxylic acid or ester groups, amide groups, sulfonic acid or ester groups, hydroxyl groups and thiol or thioester groups.

Preferably, L is a divalent $C_{1-20}$ hydrocarbon which may contain one or more heteroatoms selected from the group of an oxygen atom, a sulfur atom, and a nitrogen atom. More preferably, L is an aliphatic group in the form of a linear $C_1$ to $C_{20}$ or branched $C_3$ to $C_{20}$ alkylene group, linear $C_2$ to $C_{20}$ and branched $C_3$ to $C_{20}$ alkenylene group, $C_3$ to $C_{20}$ cycloalkylene or cycloalkenylene group which may contain 1 to 20 heteroatoms selected from oxygen, nitrogen and sulphur, which heteroatoms may be in the form described above.

According to one aspect of the invention, L is a group of the following formula (V)

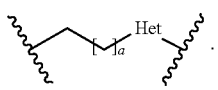

(V)

In formula (V), a is 0 or an integer of from 1 to 10, and Het is selected from the group of sulfur, oxygen, and nitrogen substituted with a hydrogen atom (NH) or a straight-chain $C_{1-6}$ alkyl group or a branched or cyclic $C_{3-6}$ alkyl group. More preferably, in formula (V), a is 0 or an integer of from 1 to 6, and Het is oxygen or NH, most preferably a is 0 or an integer of from 1 to 3, and Het is NH.

According to another aspect of the invention, L may be an alkylene(polyoxyalkylene) group. The alkylene(polyoxyalkylene) for L is not particularly limited, but preferably, it is a $C_{2-6}$ alkylene-(O—$C_{2-6}$ alkylene)k wherein k is 1 to 20. Preferably, the alkylene(polyoxyalkylene) is ethylene(polyoxyethylene) wherein k is 1 to 10, most preferably 1 to 5.

In the initiator modified polyacidic polymer (b) having repeating units of formula (I), the covalently bonded initiator compound Y and Z may independently from each other be selected from any initiator compound of the initiator system, which is described in detail below.

Preferably, in formula (I), the covalently bonded photoinitiator compound Y and Z are independently from each other selected from the group of benzophenone, 1,2-diketones, 1,3 diketones, aromatic amines, iodonium salts, and phosphines, more preferably from 1,2-diketones, aromatic amines and phosphines, most preferably from aromatic amines. At least one initiator compound is an aromatic amine initiator compound.

Preferably, in formula (I), the covalently bonded redox initiator compound Y and Z are independently from each other selected from the group comprising either one or more reducing agents or an oxidizing agent. The reducing agent may be a tertiary amine, or an organic compound containing the —$SO_2M$ group, wherein M is H or alkali metal ion, such as a sulfinic acid or an alkali metal sulfinate. The reducing agent may also be N,N-dihydroxyethyl p-toluidine, N,N-dimethyl p-toluidine, N,N-dimethylaminophenylethyl alcohol, N,N-dimethylaminophenylacetic acid, benzenesulfinic acid, toluenesulfinic acid, sodium benzenesulfinate, potassium benzenesulfinate, sodium toluenesulfinate, and/or potassium toluenesulfinate. At least one initiator compound is an aromatic amine initiator compound. The oxidizing agent may be a peroxide, such as benzoyl peroxide, hydrogen peroxide, di-t-butyl peroxide, and/or t-butyl hydrogen peroxide.

Most preferably, in formula (I), the covalently bonded initiator compound Y and Z are independently from each other selected from the following moieties of formula (II):

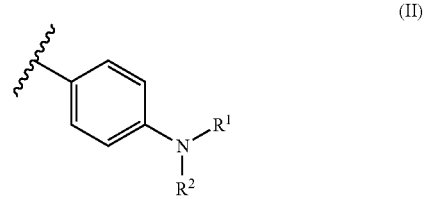

(II)

In formula (II), $R^1$ and $R^2$, which may be the same or different, independently represent a $C_{1-6}$ straight-chain, $C_{3-6}$ branched or cyclic alkyl group, preferably a $C_{1-4}$ straight-chain or branched alkyl group.

In formula (I), the covalently bonded initiator compound Y and Z may further independently from each other be selected from the following moieties of formulae (III) and (IV):

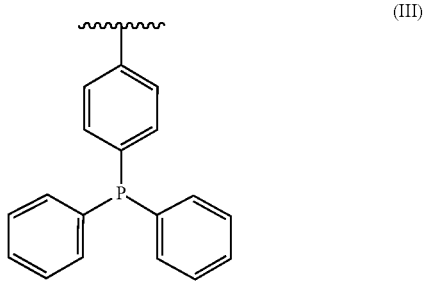

(III)

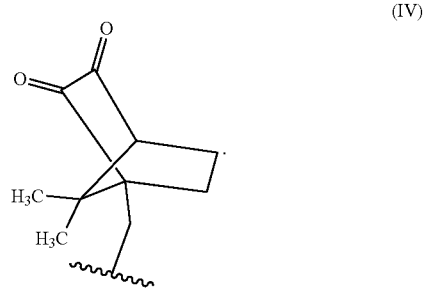

(IV)

The polyacidic polymer (b) is preferably prepared by a process comprising a step (a) of providing a precursor polyacidic polymer having repeating units of the following formula (VI)

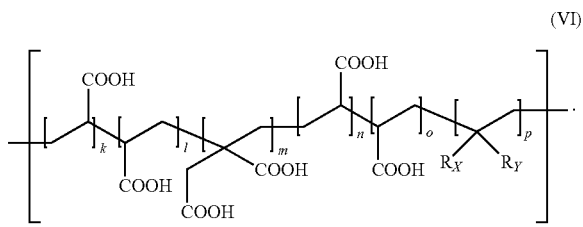

(VI)

In formula (VI), $R_X$ is OH or $NH_2$, optionally protected with a protective group, $R_Y$ is a hydrogen atom or COOH, and k+l+m+n+o+p are defined as above for formula (I). Preferably, the average molecular weight of compound of formula (VI) is 5 to 290 kDa, more preferably 7 to 270 kDa, most preferably 9 to 230 kDa.

The precursor polyacidic polymer having repeating units of the following formula (VI) may be prepared based by polymerizing acrylic acid or a mixture comprising acrylic acid.

A mixture comprising acrylic acid may further comprise one or more unsaturated monocarboxylic acids or unsaturated dicarboxylic acids or an anhydride of unsaturated dicarboxylic acids. Specific examples include itaconic acid, maleic acid, methacrylic acid, 2-chloroacrylic acid, 2-cyanoacrylic acid, aconitic acid, mesaconic acid, fumaric acid, glutaconic acid, citraconic acid, utraconic acid, and an anhydride of the unsaturated dicarboxylic acids. Preferred are itaconic acid and maleic acid, most preferred is itaconic acid.

The repeating unit having the repeating number p may be introduced in the precursor polyacidic polymer having repeating units of the following formula (VI) by polymerizing it with $R_X$ being OH or $NH_2$, or $R_X$ being OH or $NH_2$ protected with a suitable protective group. The protective group of an optionally protected OH or $NH_2$ group is not particularly limited. Any protective group for OH or $NH_2$ groups known in the art of organic chemistry may be used, as described e.g. in P. G. M. Wuts and T. W. Greene, Greene's Protective Groups in Organic Synthesis, 4th Edition, John Wiley and Sons Inc., 2007.

Furthermore, a mixture comprising acrylic acid may further comprise copolymerizable monomers which do not have a carboxylic acid functionality or an anhydride thereof, whereby it is preferable that the proportion of the unsaturated carboxylic acid units is 50% by mol or more of the entire structural units. Preferably, the precursor polyacidic polymer having repeating units of formula (VI) contains from 50 to 100 mole percent of acrylic acid repeating units.

The copolymerizable monomer is preferably an ethylenically unsaturated polymerizable monomer, and the copolymerizable monomer includes, for example, styrene, acrylamide, acrylonitrile, methyl methacrylate, vinyl chloride, allyl chloride, vinyl acetate, 1,1,6-trimethylhexamethylene dimethacrylate ester.

Among the precursor polyacidic polymers having repeating units of the formula (VI), the homopolymers of acrylic acid and copolymers of acrylic acid and itaconic acid anhydride are preferred. According to a preferred embodiment, the precursor polyacidic polymer having repeating units of the formula (VI) is polyacrylic acid or a copolymer of acrylic acid and itaconic anhydride.

The precursor polyacidic polymer having repeating units of formula (VI) provided by step (a) is reacted in a subsequent step (b) with derivatives of initiator compounds having a reactive group capable of reacting with the COOH groups of the precursor polyacidic polymer having repeating units of formula (VI). Preferably, the derivatives of initiator compound have a reactive group selected from an isocyanate group, an amine group, an alcohol group or a halogen atom selected from Cl, Br or I.

By step (b), at least one of the one or a mixture of two or more initiator compounds of the initiator system are linked to the polyacidic polymer by a covalent bond forming a initiator modified polyacidic polymer having repeating units of formula (I). Preferably, the initiator modified polyacidic polymer having repeating units of formula (I) contains 0.01 to 20 mole %, more preferably 0.05 to 10 mole % covalently bonded initiator compounds per 100 mole % of acidic groups of the initiator modified polyacidic polymer.

Preferably, the isocyanate, amine, alcohol or halogeno derivatives of one or a mixture of two or more initiator compounds are selected from compounds of the following formulae (VII), (VIII) and (IX):

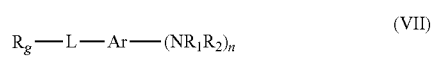

(VII)

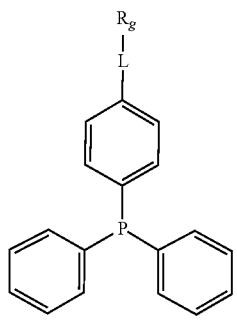

(VIII)

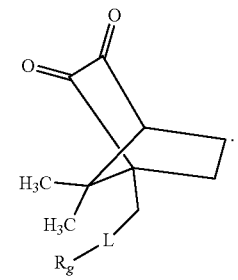

(IX)

In formulae (VII), (VIII) and (IX), L is a single bond or a divalent linker of formula (V) as defined above for formula (I), and $R_g$ is selected from an isocyanate group, an amine group, an alcohol group or a halogen atom selected from Cl, Br or I. Furthermore, in formula (VII), $R^1$ and $R^2$ have the same meaning as defined for formula (XVI), Ar represents an aromatic group, and n is 1 to 3.

In formula (VII), the aromatic group Ar may be a $C_{4-14}$ aryl group or a $C_{3-14}$ heteroaryl group containing 1 to 3 heteroatoms selected from nitrogen, oxygen and sulfur, preferably a $C_{6-10}$ aryl group or a $C_{5-9}$ heteroaryl group containing 1 or 2 nitrogen atoms. Most preferably, the aromatic groups Ar is a phenyl group, a naphtyl group or a pyridyl group. More preferably, in formula (VII), Ar is a phenyl group, and n is 1, even more preferably Ar is a phenyl group, n is 1 wherein the group $NR_1R_2$ is in para-position to L, and most preferably Ar is a phenyl group, n is 1 wherein the group $NR_1R_2$ is in para-position to L and $R_g$, L is a single bond an $R_g$ is an isocyanate group.

In formulae (VII), (VIII) and (IX), $R_g$ is preferably an isocyanate group.

According to the present invention, for linking one or more initiator compound(s) by covalent bonding in step (b) to the precursor polyacidic polymer having repeating units of the following formula (VI), preferably, it is not required that the carboxylic acid groups of the polymer are protected. Therefore, after step (b), the thus obtained initiator modified polyacidic polymer having repeating units of formula (I) can be directly used as the polyacidic polymer (b) according to the present invention without further treatment for removing protective groups.

For reacting compounds of formulae (VII), (VIII) and (IX) with $R_g$ being an isocyanate group, in step (b), a coupling agent may optionally be added for activating the carboxylic acid groups of the precursor polyacidic polymer having repeating units of formula (VI). The coupling agent is preferably added prior to the reaction with compounds of formulae (VII), (VIII) and (IX). Preferably, the coupling agent is a carbodiimide, more preferably a carbodiimide selected from N,N'-dicyclohexylcarbodiimide (DCC), N-(3-dimethylaminopropyl)-N'-ethylcarbonate (EDC), and N,N'-diisopropylcarbodiimide (DIC).

In compounds of formulae (VII), (VIII) and (IX), when $R_g$ is an isocyanate group, reacting the carboxylic acid groups of the precursor polyacidic polymer having repeating units of formula (VI) with the isocyanate derivatives of compounds of formulae (VII), (VIII) and (IX) results in a mixed acid anhydride as intermediate compound, which decarboxylates. Thereby, an N-substituted amide in the form of an initiator modified polyacidic acid having repeating units of formula (I) comprising, at least partially, X being NH—L—Z, is obtained.

Preferably 0.02 to 0.5 eq. of the one or more compounds of formulae (VII), (VIII) and (IX) are reacted with the precursor polyacidic polymer having repeating units of formula (VI) based on the total number of carboxylic acid groups of the precursor polyacidic polymer having repeating units of formula (VI).

The reaction conditions for the reaction according to step b) of the present invention are not particularly limited. Accordingly, it is possible to carry out the reaction in any suitable solvent or a suitable mixture of two or more solvents. Preferably, a solvent may be selected from the group of dioxane, dimethylformamide (DMF), acetonitrile, carbon tetrachloride, and tetrahydrofurane (THF). More preferably, dioxane, dimethylformamide (DMF), and/or acetonitrile are used, most preferably dioxane.

The reaction temperature is not particularly limited. Preferably, the reaction is carried out at a temperature of between −10° C. to the boiling point of the solvent. Preferably, the reaction temperature is in the range of from 0° C. to 100° C., more preferably 20 to 60° C., and most preferably 30 to 50° C. The reaction time is not particularly limited. Preferably, the reaction time is in the range of from 10 minutes to 120 hours, more preferably 1 hour to 80 hours, most preferably 4 to 16 hours. The reaction between the precursor polyacidic polymer having repeating units of formula (VI) and the one or more compound(s) of formulae (VII), (VIII) and (IX) may preferably be carried out at a temperature of from 30 to 50 ° C. for 4 to 16 hours.

The reaction product obtained in step b) may be isolated by precipitation, decantation and/or filtration. The product may be purified by recrystallization and/or washing with a suitable solvent.

For application of the present dental resin-modified glass ionomer composition, the polyacidic polymer (b) is combined with the reactive particulate filler (a). In this context, "combining" means physical mixing of the components and the association of the components such that the physical mixing of the components is facilitated, preferably in a single step. Accordingly, the polyacidic polymer (b) and the reactive particulate filler (a) may be combined in a kit-of-parts or two- or multi-pack composition, wherein the polyacidic polymer (b) and the reactive particulate filler (a) are separated for storage.

Besides of the above described initiator compounds linked to the initiator modified polyacidic polymer by a covalent bond, the dental resin-modified glass ionomer composition may, alternatively or additionally, comprise one or a mixture of two or more further initiator compounds other than the above described ones of formulae (II), (III) or (IV). These further initiator compounds may be covalently linked to the initiator modified polyacidic polymer, or they may be contained in the dental cement composition as discrete components.

The photoinitiator system consists of one or more initiator compounds generating alone or in combination free radicals when irradiated with light having a wavelength in the range of from 400 to 800 nm.

As initiator compounds, any compound capable of initiating a polymerization reaction by irradiation with light may be suitably used for making the present dental resin-modified glass ionomer composition curable. The term "curable" refers to dental resin-modified glass ionomer composition that will polymerize into a crosslinked polymer network when irradiated with light, whereby (co)polymerizable monomers, oligomers and even polymerizable polymers polymerize into a polymer network.

For example, a suitable photoinitiator system may be in the form of a binary or tertiary system. A binary system may include a photoinitiator and an electron donor compound. A tertiary system may include a photoinitiator, an electron donor compound and a coinitiator, as for example described in U.S. Pat. No. 5,545,676.

Suitable photoinitiators for the photoinitiator system are Nourish type I and Nourish type II photoinitiators.

The term "Norrish type I" refers to a photoinitiator undergoing excitation by energy absorption with subsequent decomposition of the compound into one or more radicals.

The term "Norrish type II" refers to a photoinitiator undergoing excitation, and the excited photoinitiator interacts with a second compound, such as an electron donor, a coinitiator or a sensitizer, by either energy transfer or a redox reaction to form free radicals from any of the compounds.

Suitable Norrish type I photoinitiators are for example phosphine oxides or Si- or Ge-acyl compounds.

Phosphine oxide photoinitiators may have a functional wavelength range of about 380 nm to about 450 nm, which include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethmbenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Suitable Si- or Ge-acyl compounds preferably have the following formula (X):

$$X—R^9 \quad (X)$$

wherein

X is a group of the following formula (XI):

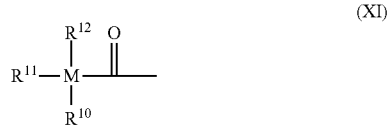

(XI)

wherein

M is Si or Ge;

$R^{10}$ represents a substituted or unsubstituted hydrocarbyl or hydrocarbylcarbonyl group;

$R^{11}$ represents a substituted or unsubstituted hydrocarbyl or hydrocarbylcarbonyl group;

$R^{12}$ represents a substituted or unsubstituted hydrocarbyl group; and $R^9$ i) has the same meaning as X, whereby the compound of formula (X) may be symmetrical or unsymmetrical; or ii) is a group of the following formula (XII):

(XII)

wherein

Y represents a single bond, an oxygen atom or a group NR', wherein R' represents a substituted or unsubstituted hydrocarbyl group;

$R^{13}$ represents a substituted or unsubstituted hydrocarbyl group, a trihydrocarbylsilyl group, a mono(hydrocarbyl-carbonyl)dihydrocarbylsilyl group or a di(hydrocarbyl-carbonyl)mono-hydrocarbylsilyl group.

It was surprisingly found that Si- or Ge-acyl compounds of formula (X) represent 1,2-diketone photoinitiators which are particularly suitable for dental compositions. With compounds of formula (X), a high polymerization efficiency is attained, and no coloration problems occur, or in a polymerization system comprising a conventional photoinitiator such as camphor quinone, coloration is efficiently suppressed. Furthermore, compounds of formula (X) have a light absorption within the wavelength range typically applied in dental application, they are compatible with the ingredients of dental compositions and besides, they are considered physiologically harmless.

In connection with the Si- or Ge-acyl compound of formula (X), the term "substituted" as used herein means that $R^{10}$, $R^{11}$, $R^{12}$, $R^{13}$ and R' may be substituted by a substituent selected from the group consisting of halogen atoms, a nitro group, a cyano group, a hydroxy group, an amino group, $C_{1-6}$ alkyl groups, $C_{1-6}$ alkoxy groups and a —$NR^xR^y$ group wherein $R^x$ and $R^y$ independently from each other represent a $C_{1-6}$ alkyl group. Here, illustrative of the halogen atoms can be fluorine, chlorine, bromine and iodine. The $C_{1-6}$ alkyl groups are, for example, methyl, ethyl, n-propyl, isopropyl and n-butyl. Illustrative of the $C_{1-6}$ alkoxy groups are, for example, methoxy, ethoxy and propoxy. The alkyl moieties in these substituents may be linear, branched or cyclic. Preferably, the substituent is selected from a chlorine atom, a nitro group, a $C_{1-4}$ alkoxy group and a —$NR^xR^y$ group wherein $R^x$ and $R^y$ independently from each other represent a $C_{1-4}$ alkyl group.

if $R^{10}$, $R^{11}$ and $R^{12}$ are substituted, then it is preferred that they are substituted with 1 to 3 substituents, more preferably with 1 substituent.

In the compound of formula (X), moieties $R^{10}$, $R^{11}$ and $R^{12}$ may be defined as follows:

$R^{10}$ and $R^{11}$ independently from each other represent a substituted or unsubstituted hydrocarbyl or hydrocarbylcarbonyl group, and $R^{12}$ represents a substituted or unsubstituted hydrocarbyl group.

The hydrocarbyl group may be an alkyl group, a cycloalkyl group, a cycloalkylalkyl group, an arylalkyl group or an aryl group.

An alkyl group may be straight-chain or branched $C_{1-20}$ alkyl group, typically a $C_{1-8}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{3-8}$ cycloalkyf group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(-) group can for example, include methylcyclopropyl(-) methylcyclobutyl(-), methylcyclopentyl(-), methylcyclohexyl(-), ethylcyclopropyl(-), ethylcyclobutyl(-), ethylcyclopentyl(-), ethylcyclohexyl(-), propylcyclopropyl (-), propylcyclobutyl(-), propylcyclopentyl(-), propylcyclohexyl(-).

An arylalkyl(-) group may be a $C_{7-20}$ arylalkyl(-) group, typically a combination of a linear or branched alkyl group having 1 to 6 carbon atoms and an aryl(-) group having 6 to 10 carbon atoms. Specific examples of an arylalkyl(-) group are a benzyl(-) group or a phenylethyl(-) group.

An aryl group can include aryl groups having 6 to 10 carbon atoms. Examples of the aryl group are phenyl and naphtyl.

The hydrocarbylcarbonyl groups of $R^{10}$ and $R^{11}$ represent acyl groups ($R_{org}$—(C=O)—) in which the organic residue $R_{org}$ is a hydrocarbyl residue as defined above.

Compound of formula (X) may contain one or two hydrocarbylcarbonyl groups, that is either one of $R^{10}$ or $R^{11}$ is a hydrocarbylcarbonyl group, or both $R^{10}$ and $R^{11}$ are hydrocarbylcarbonyl groups. Preferably, compound of formula (V) contains one hydrocarbylcarbonyl group.

Preferably, the hydrocarbylcarbonyl group is an arylcarbonyl group, more preferably a benzoyl group.

Preferably, $R^{10}$ and $R^{11}$ are independently selected from the group consisting of a straight chain or branched $C_{1-6}$ alkyl group, and a phenyl or benzoyl group which may optionally be substituted by one to three substitutents selected from halogen atoms, a nitro group, a $C_{1-4}$ alkoxy group and a $-NR^xR^y$ group wherein $R^x$ and $R^y$ independently from each other represent a $C_{1-4}$ alkyl group, and $R^{12}$ is a straight chain or branched $C_{1-6}$ alkyl group or a phenyl group.

Most preferably, $R^{10}$ and $R^{11}$ are independently selected from the group consisting of a straight chain or branched $C_{1-4}$ alkyl group, and a phenyl or benzoyl group which may optionally be substituted with one substituent selected from the group consisting of selected from a halogen atom, a nitro group, a $C_{1-4}$ alkoxy group and a $-NR^xR^y$ group wherein $R^x$ and $R^y$ independently from each other represent a $C_{1-4}$ alkyl group, and $R^{12}$ is a straight chain or branched $C_{1-4}$ alkyl group.

In the compound of formula (X), $R^9$ may have the same meaning as X, whereby the compound of formula (X) may be symmetrical or unsymmetrical. Alternatively, $R^9$ may represent a substituted or unsubstituted hydrocarbyl group, or a group of formula (XII). Preferably, if $R^9$ has the same meaning as X, then compound of formula (X) is unsymmetrical. If $R^9$ represents a substituted or unsubstituted hydrocarbyl group, then the hydrocarbyl group has the same meaning as defined above for $R^{10}$ and is independently selected therefrom.

In the group of formula (XII) of compound of formula (X), $R^{13}$ represents a substituted or unsubstituted hydrocarbyl group, a trihydrocarbylsilyl group, a mono(hydrocarbylcarbonyl)-dihydrocarbylsilyl group or a di(hydrocarbylcarbonyl)monohydrocarbylsilyl group.

If $R^{13}$ of formula (XII) is a trihydrocarbylsilyl group, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^{10}$, $R^{11}$ and $R^{12}$ and is independently selected therefrom.

In formula (XII), R' has the same meaning as defined for $R^{12}$ and is independently selected therefrom.

For example, compounds of formula (X) wherein $R^9$ has the same meaning as X and which are symmetrical may be have the following structural formulae:

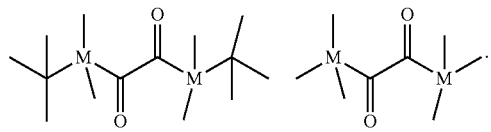

For example, compounds of formula (X) wherein $R^9$ represents a group of formula (XII) wherein Y is a bond, an oxygen atom or a NR' group, and $R^{13}$ represents a substituted or unsubstituted hydrocarbyl group may have the following structural formulae:

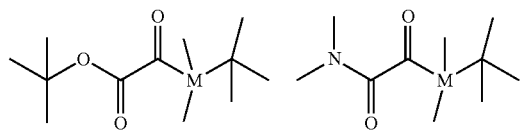

-continued

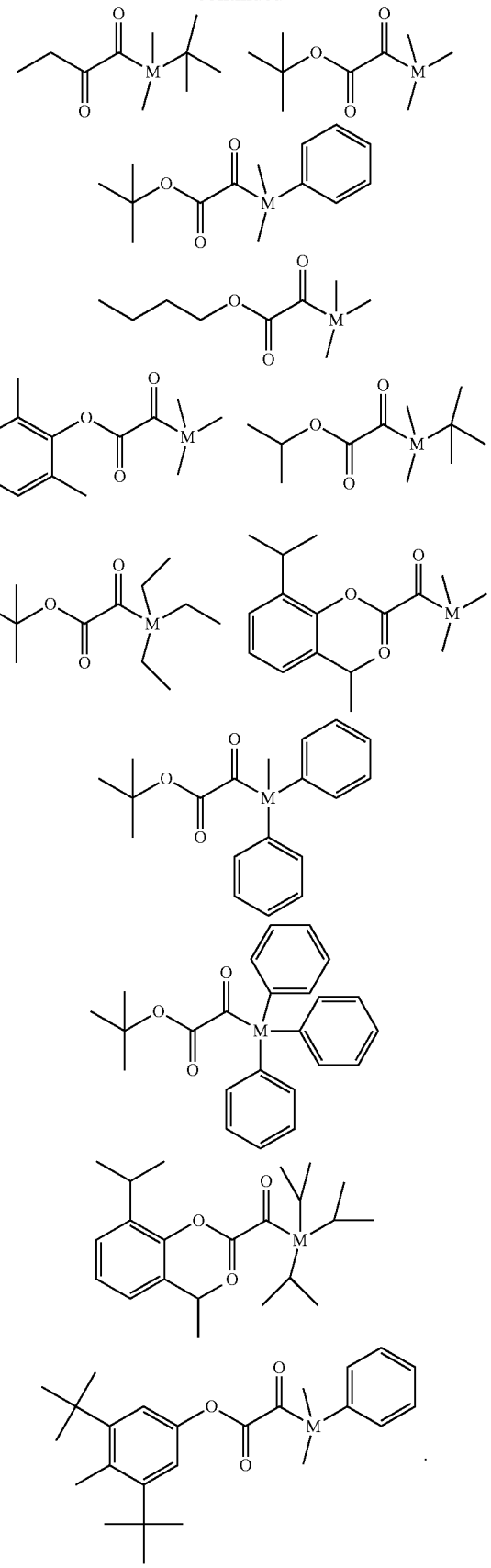

For example, compounds of formula (X) wherein $R^9$ represents a group of formula (XII) wherein $R^{13}$ represents a trihydrocarbylsilyl group have the following structural formulae:

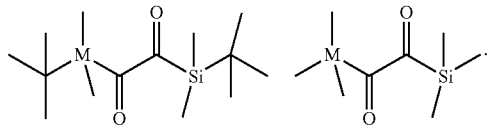

Preferably, compound of formula (X) is selected from the group consisting of:

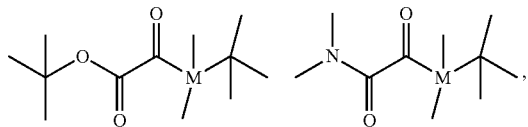

wherein compounds of formula (X) with M=Si are particularly preferred.

More preferably, compound of formula (X) has the following structural formula:

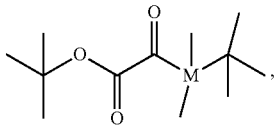

wherein it is particularly preferred that M=Si. That is, tert-butyl (tert-butyldimethylsilyl)-glyoxylate) (DKSi) is particularly preferred.

In case the photocurable dental composition is in the form of an acidic composition, that is a composition having a pH of less than 7, depending on the composition's pH level, it is preferred to select compounds of formula (X) with the proviso that they do not contain ester groups, or at least only ester groups which do not significantly hydrolyse in aqueous media at pH 3 at room temperature within one month. Thereby, an advantageous stability of an acidic photocurable dental composition, that is a composition having a pH of less than 7, in terms of shelf-life stability of the uncured photocurable dental composition as well as stability after curing in the mouth of a patient is ensured. Therefore, for acidic photocurable dental compositions, particularly preferred are compounds of formula (X) excluding $R^9$ being a group of formula (XII) in which Y is an oxygen atom.

Furthermore, since the acylsilyl moiety (—C(=O)—Si—) might be sensitive to basic conditions, that is a pH higher than 7, it is preferred to suitably select a pH value of the composition being higher than 7 with the proviso that the acylsilyl moiety is not cleaved in aqueous media at the selected basic pH at room temperature within one month.

The compound of the formula (X) may be a known compound which is commercially available or a may be prepared according to published procedures, as described for example in WO 2017/060459 A1.

Suitable Norrish type II photoinitiators may be selected from the group consisting of camphorquinone, benzil, 2,2'-3 3'- and 4,4'-dihydroxylbenzil, 2,3-butanedione, 2,3-pentanedione, 2,3-hexanedione, 3,4-hexanedione, 2,3-heptanedione, 3,4-heptanedione, 2,3-octanedione, 4,5-octanedionefuril, biacetyl, 1,2-cyclohexanedione, 1,2-naphthaquinone, and acenaphthaquinone. Camphorquinone is preferred.

Particularly preferred photoinitiators, irrespective whether Norrish type I or II, include 1,2-diketones having a light absorption within a range of about 400 nm to about 520 nm, preferably, about 450 to about 500 nm.

Preferably, irrespective whether Norrish type I or II, the photoinitiator is a 1,2-diketone, even more preferably camphor quinone or a Si- or Ge-acyl compound of formula (X), yet even more preferably camphor quinone or DKSi, and most preferably camphor quinone.

According to one preferred embodiment, the photoinitiator system consists of a Norrish type I photoinitiator covalently linked to the polyacidic polymer.

According to another preferred embodiment, the photoinitiator system consists of a Norrish type II photoinitiator comprising an electron donor component, a coinitiator component or a sensitizer component, wherein the electron donor component, the coinitiator component or the sensitizer component is covalently linked to the polyacidic polymer, and the other components are contained in the dental cement composition or covalently linked to the polyacidic polymer.

Preferred electron donor components include, for example, amines, amides, ethers, thioethers, ureas, thioureas, ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid or an organic hydride of Si, Ge or Sn.

More preferably, the electron donor component is an amine compound or an organic hydride compound of Si, Ge or Sn.

Preferred amine compounds are tertiary amine compounds, more preferably tertiary amine compounds selected from the group consisting of triethanolamine, 4-N,N-dimethylaminobenzonitrile, methyl N,N-dimethylaminobenzoate, ethyl N,N-dimethylaminobenzoate, N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene. Most preferably, the tertiary amine compound is selected from the group consisting of triethanolamine, methyl 4-N,N-dimethylaminobenzoate, ethyl 4-N,N-dimethylaminobenzoate, 4-N,N-dimethylaminoethyl methacrylate and isoamyl 4-N,N-dimethylaminobenzoate.

Preferred organic hydrides of Si, Ge or Sn have the following formula (XIII):

wherein L* is a moiety of the following formula (XIV)

In formula (XIV), X* represents Si, Ge, or Sn, $R^a$ represents a hydrogen atom, an organic moiety or a different moiety L*, and $R^b$ and $R^c$, which are independent from each other, represent an organic moiety.

The organic metal hydride of formula (XIII) may react as a hydrogen donating agent in a photoexcitation complex with the alpha-diketone sensitizer. Accordingly, when an alpha-diketone absorbs visible light and forms an exciplex with the organic metal hydride of formula (XIII), a hydrogen transfer may take place from the organic metal hydride to the alpha-diketone compound, whereby the organic metal hydride of formula (XIII) is transformed into a radical specifies capable of facilitating the polymerization reaction.

In formula (XIV), X* represents Si, Ge, or Sn. Preferably, X* represents Si or Ge. More preferably, X* is Ge. According to a specific embodiment, compound of formula (XIII) is a silane compound. According to a further specific embodiment, compound of formula (XIII) is a germane compound.

In formula (XIV), $R^a$ may be a hydrogen atom, an organic moiety or a different moiety L. When $R^a$ is a hydrogen atom, then the compound of formula (XIII) contains two metal hydride bonds (X*—H). In case $R^a$ is a hydrogen atom, the X* is Si.

When $R^a$ is an organic moiety, $R^a$ is preferably an aromatic, an aliphatic or an alicyclic group. An aromatic group may be a phenyl group. The phenyl group may be substituted by one or more straight chain or branched alkyl groups having 1 to 6 carbon atoms, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

When Ra is a different moiety L*, the compound of formula (XIII) of the formula (XIII) contains a metal-metal bond. In case two moieties L* are present, then each X*, Ra, $R^b$ and $R^c$ may be the same or different and independently has the meaning as defined by the present invention.

$R^b$ and $R^c$ which are independent from each other, represent an organic moiety. An organic group may be an aromatic, an aliphatic or an alicyclic group. An aromatic group may be a phenyl group. The phenyl group may be substituted by one or more straight chain or branched alkyl groups having 1 to 6 carbon atoms, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

According to a preferred embodiment, $R^a$, $R^b$, and $R^c$ in the compound of formula (XIII) of formula (XIII) are the same and represent an aliphatic, an aromatic or an alicyclic hydrocarbon group.

According to a preferred embodiment, the compound of formula (XIII) of formula (XIII) is a compound of the following formula:

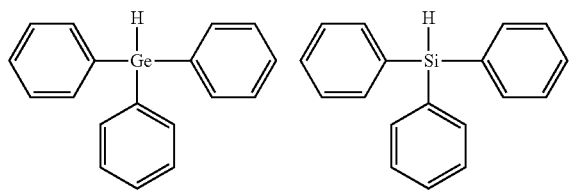

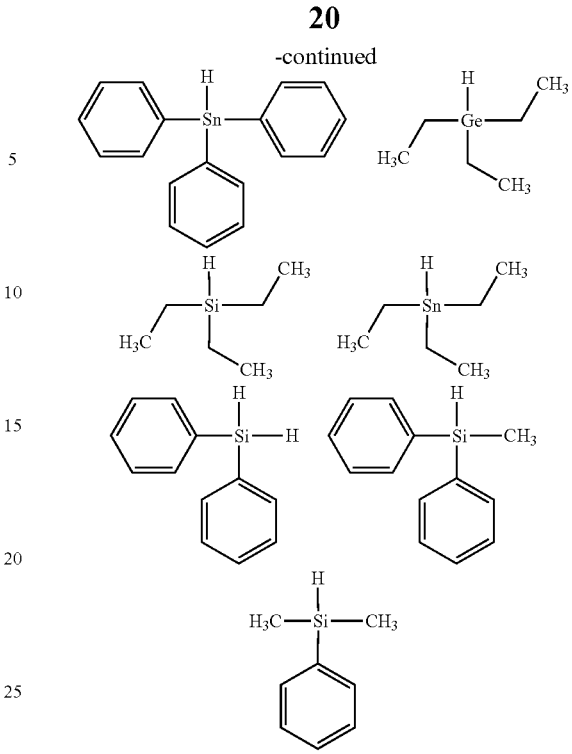

According to a preferred embodiment, the dental resin-modified glass ionomer composition contains the compound of formula (VIII) in an amount from 0.05 to 5 percent by weight based on the total weight of the composition.

Coinitiator components are preferably selected from iodonium salts, sulfonium salts, phosphonium salts and tertiary aromatic phosphine compounds.

Preferred iodonium, sulfonium or phosphonium salts respectively have a cation selected from:

(1) an iodonium ion of the following formula (XVII):

(XVII)

wherein
$R^3$ and $R^4$ which are independent from each other represent an organic moiety;

(2) a sulfonium ion of the following formula (XVIII):

(XVIII)

wherein
$R^5$, $R^6$ and $R^7$ which are independent from each other, represent an organic moiety, and optionally any two of $R^5$, $R^6$ and $R^7$ form a cyclic structure together with the sulfur atom to which they are bound;

(3) a phosphonium ion of the following formula (XIX):

(XIX)

wherein
$R^8$, $R^9$ and $R^{10}$ which are independent from each other, represent an organic moiety.

Salts having a cation selected from formulae (XVII), (XVIII) and (XIX) represent particularly efficient iodonium, sulfonium or phosphonium salts and significantly improve the polymerization performance of the photoinitiator system.

Preferably, $R^3$ and $R^4$ of the iodonium ion of formula (XVII), $R^5$, $R^6$ and $R^7$ of the sulfonium ion of (XVIII), and $R^8$, $R^9$ and $R^{10}$ of the phosphonium ion of formula (XIX) are respectively selected from an aromatic, an aliphatic or an alicyclic group. An aromatic group may be a phenyl group.

The phenyl group may be substituted by one or more straight chain or branched alkyl groups having 1 to 6 carbon atoms, straight chain or branched alkoxy groups having 1 to 6 carbon atoms, aromatic groups such as aryl groups or aryloxy groups, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

More preferably, $R^3$ and $R^4$ of the iodonium ion of formula (XVII) and $R^5$, $R^6$ and $R^7$ of the sulfonium ion of (XVIII) are respectively selected from a phenyl group which may be substituted with 1 to 3 substituents selected from halogen atoms, a cyano group, a hydroxy group, an amino group, $C_{1-6}$ alkyl groups and $C_{1-6}$ alkoxy groups. Preferably, R' is a linear, branched or cyclic alkyl group having 1 to 6 carbon atoms, which may be substituted with 1 to 3 groups selected from halogen atoms, a cyano group, a hydroxy group, an amino group, $C_{1-6}$ alkyl groups and $C_{1-6}$ alkoxy groups.

According to a preferred embodiment, the iodonium ion of formula (XVII) is a diaryl iodonium ion. Examples of useful diaryl iodonium ions include (4-methylphenyl)[4-(2-methylpropyl)phenyl]iodonium, diphenyliodonium tetrafluoroborate, di(4-methylphenyl)iodonium, phenyl-4-methylphenyliodonium, di(4-heptylphenyl)iodonium, di(3-nitrophenyl)iodonium, di(4-chlorophenyl)iodonium, di(naphthyl)iodonium, di(4-trifluoromethylphenyl)iodonium, diphenyliodonium, di(4-methylphenyl)iodonium; diphenyliodonium, di(4-phenoxyphenyl)iodonium, phenyl-2-thienyliodonium, 3,5-dimethylpyrazolyl-4-phenyliodonium, diphenyliodonium, 2,2'-diphenyliodonium, di(2,4-dichlorophenyl)iodonium, di(4-bromophenyl)iodonium, di(4-methoxyphenyl)iodonium, di(3-carboxyphenyl)iodonium, di(3-methoxycarbonylphenyl)iodonium, di(3-methoxysulfonylphenyl)iodonium, di(4-acetamidophenyl)iodonium, di(2-benzothienyl)iodonium, and diphenyliodonium.

More preferably aromatic iodonium ions of formula (XVII) are selected from the group consisting of diaryliodonium, (4-methylphenyl)[4-(2-methylpropyl)phenyl]iodonium, 4-octyloxyphenyl phenyliodonium, and 4-(1-methylethyl)phenyl 4-methylphenyliodonium. Most preferably, the aromatic iodonium ion of formula (XVII) is diphenyliodonium or (4-methylphenyl)[4-(2-methylpropyl)phenyl]iodonium.

A preferred sulfonium ion of formula (XVIII) is S-(phenyl)thianthrenium of the following formula:

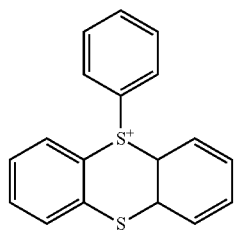

Preferably, in a phosphonium ion of formula (XIX), $R^8$, $R^9$ and $R^{10}$ independently from each other represent an aliphatic group, more preferably a straight chain or branched alkyl group having 1 to 6 carbon atoms which may be substituted by one or more aromatic groups, alicyclic groups having 3 to 6 carbon atoms, halogen atoms, hydroxyl groups or amino groups. More preferably, in a phosphonium ion of formula (XIX), $R^8$, $R^9$ and $R^{10}$ independently from each other represent a straight chain or branched alkyl group having 1 to 4 carbon atoms which may be substituted by one or more halogen atoms, hydroxyl groups or amino groups.

A particularly preferred phosphonium ion of formula (XIX) is tetrakis-(hydroxymethyl)-phosphonium (THP).

In the iodonium, sulfonium or phosphonium salts having a cation of formula (XVII), (XVIII) or (XIX), the anion may be selected from hexafluoroantimonate, trifluoromethylsulfate, hexafluorophosphate, tetrafluoroborate, hexafluoroarsenate, and tetraphenylborate. Preferred aromatic tertiary phosphine compounds have, the following formula (I):

$$Z^P-R^P \qquad (XV)$$

wherein
$Z^P$ is a group of the following formula (XVI)

$$R^*(Ar^P)P- \qquad (XVI)$$

wherein
R* represents a substituted or unsubstituted hydrocarbyl group;
$Ar^P$ represents a substituted or unsubstituted aryl or heteroaryl group;
$R^P$ is an aryl group, which may be substituted by one or more groups selected from a hydroxyl group, an amino group, a —$NR^aR^b$ group (wherein $R^a$ and $R^b$, which may be the same or different, are selected from $C_{1-6}$ alkyl groups), a carboxyl group, and a group having a polymerizable double bond;
wherein the group R* and $Ar^P$ may be substituted by one or more groups selected from a hydroxyl group, an oxo group, a —$NR^aR^b$ group (wherein $R^a$ and $R^b$, which may be the same or different, are selected from a hydrogen atom and $C_{1-6}$ alkyl groups), a carboxyl group, and a group having a polymerizable double bond, and
$L^P$ may be substituted by one or more groups selected from a hydroxyl group, an oxo group, a —$NR^aR^b$ group (wherein $R^a$ and $R^b$, which may be the same or different, are selected from a hydrogen atom and $C_{1-6}$ alkyl groups), a carboxyl group, and a group having a polymerizable double bond, In formula (XV), for R*, the monovalent hydrocarbyl group may be an alkyl group, a cycloalkyl group, a cycloalkylalkyl group, an arylalkyl group or an aryl group.

$Ar^P$ represents a substituted or unsubstituted aryl or heteroaryl group. An aryl group may be selected from a phenyl group, a naphtyl group, a tolyl group, a xylyl group, and a styryl group. A heteroaryl group may be a pyridyl group.

$L^P$ is a substituted or unsubstituted divalent hydrocarbyl group which may contain a linkage selected from an ether linkage, a thioether linkage, an ester linkage, an amide linkage, and a urethane linkage. For $L^P$, the divalent hydrocarbyl group may be an alkyldiyl group, a cycloalkyldiyl group, a cycloalkylalkyl-diyl group, an arylalkyl-diyl group or an aryldiyl group. In a cycloalkylalkyl-diyl, one valency may be bonded to each of the cycloalkyl moiety or the alkyl moiety, or both valencies may be bonded to either the cycloalkyl moiety or the alkyl moiety. In a arylalkyl-diyl group, each of the aryl moiety or the alkyl moiety may be monovalent respectively, or either the aryl moiety or the alkyl moiety is divalent, while the other moiety is nonvalent. In a cycloalkylalkyl-diyl, each of the cycloalkyl moiety or the alkyl moiety may be monovalent respectively, or either the cycloalkyl moiety or the alkyl moiety is divalent, while the other moiety is nonvalent.

The following definitions apply both for the monovalent and the divalent hydrocarbyl group, therefore, for the definition of the divalent hydrocarbyl group, the suffixes "diyl" and "-diyl" are bracketed.

An alkyl(diyl) group may be straight-chain or branched $C_{1-20}$ alkyl(diyl) group, typically a $C_{1-8}$ alkyl(diyl) group. Examples for a $C_{1-6}$ alkyl(diyl) group can include linear or branched alkyl(diyl) groups having 1 to 6 carbon atoms, preferably 1 to 4 carbon atoms, for example, methyl(diyl), ethyl(diyl), n-propyl(diyl), isopropyl(diyl), n-butyl(diyl), isobutyl(diyl), sec-butyl(diyl), tert-butyl(diyl), n-pentyl (diyl), isopentyl(diyl) and n-hexyl(diyl).

A cycloalkyl(diyl) group may be a $C_{3-20}$ cycloalkyl(diyl) group. Examples of the cycloalkyl(diyl) group can include those having 3 to 14 carbon atoms, for example, cyclopropyl (diyl), cyclobutyl(diyl), cyclopentyl(diyl) and cyclohexyl (diyl). A cycloalkylalkyl(diyl) group can include those having 4 to 20 carbon atoms.

A cycloalkylalkyl(-diyl) group include a combination of a linear or branched alkyl(diyl) group having 1 to 6 carbon atoms and a cycloalkyl(diyl) group having 3 to 14 carbon atoms. Examples of the cycloalkylalkyl(-diyl) group can for example, include methylcyclopropyl(-diyl) methylcyclobutyl(-diyl), methylcyclopentyl(-diyl), methylcyclohexyl(-diyl), ethylcyclopropyl(-diyl), ethylcyclobutyl(-diyl), ethylcyclopentyl(-diyl), ethylcyclohexyl(-diyl), propylcyclopropyl(-diyl), propylcyclobutyl(-diyl), propylcyclopentyl(-diyl), propylcyclohexyl(-diyl).

An arylalkyl(-diyl) group may be a $C_{7-20}$ arylalkyl(-diyl) group, typically a combination of a linear or branched alkyl(diyl) group having 1 to 6 carbon atoms and an aryl(-diyl) group having 6 to 10 carbon atoms. Specific examples of an arylalkyl(-diyl) group are a benzyl(-diyl) group or a phenylethyl(-diyl) group.

An aryl(diyl) group can include aryl(diyl) groups having 6 to 10 carbon atoms. Examples of the aryl(diyl) group are phenyl(diyl) and naphtyl(diyl). Aryl(diyl) groups may contain 1 to 3 substituents. Examples of such substituents can include halogen atoms, a cyano group, a hydroxy group, an amino group, $C_{1-6}$ alkyl groups and $C_{1-6}$ alkoxy groups. Here, illustrative of the halogen atoms can be fluorine, chlorine, bromine and iodine. The $C_{1-4}$ alkyl(diyl) groups are, for example, methyl(diyl), ethyl(diyl), n-propyl(diyl), isopropyl(diyl) and n-butyl(diyl). Illustrative of the $C_{1-4}$ alkoxy(diyl) groups are, for example, methoxy(diyl), ethoxy (diyl) and propoxy(diyl). The alkyl(diyl) moieties in these substituents may be linear, branched or cyclic.

Preferably, the hydrocarbyl group is an aryl(diyl) group selected from a phenyl(diyl) group and a naphthyl(diyl) group, which groups may optionally be substituted by one to three groups selected from halogen atoms, a cyano group, an amino group, a hydroxy group, $C_{1-6}$ alkyl groups and $C_{1-6}$ alkoxy groups, or wherein the hydrocarbyl group is a non-aromatic hydrocarbyl group selected from a straight chain or branched alkyl group, a straight chain or branched alkenyl group, or a straight chain or branched alkynyl group.

The $C_{1-8}$ alkyl(diyl) group and the $C_{3-14}$ cycloalkyl(diyl) group may optionally be substituted by one or more members of the group selected from a $C_{1-4}$ alkyl group, $C_{1-4}$ alkoxy group, a phenyl group, and a hydroxy group. Examples for a $C_{1-4}$ alkyl group can include linear or branched alkyl groups having 1 to 4 carbon atoms, for example, methyl, ethyl, n-propyl, isopropyl, n-butyl, isobutyl, sec-butyl, tert-butyl. Examples for an $C_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Moreover, in formula (XV), any of the hydrocarbyl group may be substituted by one or more groups selected from halogen atoms, a cyano group, an amino group or a hydroxy group. Accordingly, in the hydrocarbyl groups some or all hydrogen atoms are replaced by halogen atoms (e.g., fluoro, bromo, chloro), for example, halo-substituted alkyl groups such as chloromethyl, chloropropyl, bromoethyl and trifluoropropyl, and cyanoethyl.

In case the hydrocarbyl group contains an alkyl(diyl) chain, one or more carbon atoms in the alkyl(diyl) chain may be replaced by an oxygen atom, a sulfur atom, an amide group, an ester group, or a urethane group. In case the hydrocarbyl group is an alkyl group having more than one carbon atom, the alkyl group contains an alkylene. Accordingly, in case the hydrocarbyl group is an n-hexyl group, any of the carbon atoms of the alkylene chain excluding the terminal methyl group may be replaced by an oxygen atom, a sulfur atom, an amide group, an ester group, a urethane group or an NH group. Therefore, the following groups may be given as specific examples in case of one or more oxygen atoms:

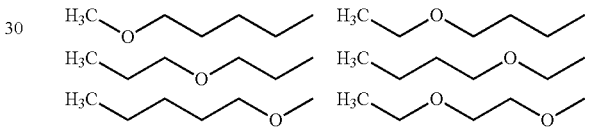

In formula (XV), group R* and/or $Ar^P$ as well as $R^P$ and/or may be substituted with a polymerizable double bond, preferably a carbon-carbon double bond. Examples of polymerizable carbon-carbon double bonds include vinyl, conjugated vinyl, allyl, acryl, methacryl and styryl. Preferably, the polymerizable double bond is selected from the group consisting of methacryl, acryl and styryl. More preferably, the double bond is styryl.

Preferably, R* and $Ar^P$ independently are aromatic hydrocarbyl groups selected from a phenyl group, a naphtyl group, a tolyl group, a xylyl group, and a styryl group.

As regards R, this moiety is an aryl group, which may be substituted by one or more groups selected from a hydroxyl group, an amino group, a —NRaRb group (wherein Ra and Rb, which may be the same or different, are selected from $C_{1-6}$ alkyl groups), a carboxyl group, and a group having a polymerizable double bond. According to a preferred embodiment, RP is an aryl group substituted by one or more groups selected from a hydroxyl group, an amino group, a —NRaRb group (wherein Ra and Rb, which may be the same or different, are selected from $C_{1-6}$ alkyl groups), a carboxyl group, and a group having a polymerizable double bond. More preferably, $R^P$ is a phenyl group substituted by one or two groups selected from a hydroxyl group, an amino group, a —NRaRb group (wherein Ra and Rb, which may be the same or different, are selected from $C_{1-6}$ alkyl groups), a carboxyl group, and a group having a polymerizable double bond.

Even more preferably, the aromatic phosphine compound is a compound of formula (XV) wherein $Z^P$ is a group of the following formula:

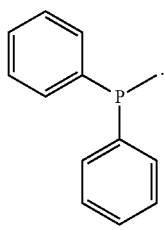

Specific examples for a compound of formula (XV) include triphenyl phosphine (TPP), 4-(diphenylphosphino) styrene (DPPS), 4-(diphenylphosphino)benzoic acid, 4-(diphenyl-phosphino) benzoic acid, 3-(diphenylphophonino) propionic acid, (4-(diphenylphosphino) N,N''-dimethylaniline, 2,2'-bis(diphenylphosphino)benzophenone (BDPPEP), bis[2-(diphenylphosphino)phenyl]ether (BDPPE), (4-Hydroxyphenyl)diphenylphosphine, allyldiphenylphosphine. Preferably, the compound of formula (XV) is triphenyl phosphine (TPP) or 4-(diphenylphosphino)styrene (DPPS), more preferably 4-(diphenylphosphino)styrene (DPPS).

From the above listed aromatic tertiary compounds of formula (XV), 4-(diphenylphosphino)styrene (DPPS) is particularly preferred, since this compound provides for particularly improved photo-bleaching results compared to the already advantageous results obtained with triphenyl phosphine (TPP).

A compound of the formula (XV) may be a known compound which is commercially available or may be prepared according to published procedures, as described for example in WO/2016/156363 A1.

Besides of a photoinitiator and the optional electron donor component and/or coinitiator component, the photoinitiator system may further contain a sensitizer component.

The sensitizer component may be selected from a Norrish type I or II photoinitiator as described above. The sensitizer component represents an additional photoinitiator other than the photoinitiator of the photoinitiator system.

According to a preferred embodiment, the dental resin-modified glass ionomer composition contains a redox initiator. The term "redox initiator" means a combination of an oxidizing agent and a reducing agent, and optionally a catalyst such as a metal salt. The redox initiator provides a redox reaction in which radicals are formed. These radicals initiate polymerisation of a radically polymerizable compound. Typically, a redox initiator system is activated by mixing the components of the redox initiator system, including by bringing the redox initiator system in contact with water and/or an organic solvent providing for at least partial dissolution of the oxidising agent and the reducing agent. A mixture of the photoinitiator system and a redox initiator is a "dual cure initiator system".

A suitable redox initiator system comprises reducing and oxidizing agents, which produce free-radicals capable of initiating polymerization of the polymerizable double bonds of monomer (c) and/or crosslinker (d), independent from the presence of light. The reducing and oxidizing agents are selected such that the dental resin-modified glass ionomer composition is sufficiently storage-stable and free of undesirable colorization to permit storage and use under typical dental conditions. Moreover, the reducing and oxidizing agents are selected so that the dual cure initiators system is sufficiently miscible with the resin system to permit dissolution of the redox initiator system in the composition.

Useful reducing agents include ascorbic acid, ascorbic acid derivatives, and metal complexed ascorbic acid compounds as described in U.S. Pat. No. 5,501,727; amines, namely tertiary amines, preferably tertiary aromatic amines such as 4-tert-butyl dimethylaniline; aromatic sulfinate salts such as p-toluenesulfinate salts and benzenesulfinate salts, most preferably sodium para-toluenesulfinate; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (III) chloride, ferrous chloride, ferrous sulfate, hydrazine, hydroxylamine, salts of a dithionite or sulfite anion, and mixtures thereof.

Suitable oxidizing agents include persulfuric acid and salts thereof, such as ammonium, sodium, potassium, cesium, and alkyl ammonium salts, preferably inorganic peroxodisulfate salts, most preferably potassium peroxodisulphate. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

A particularly preferred redox initiator contains (i) an inorganic peroxodisulphate salt, (ii) an aromatic amine, and (iii) an aromatic sulfinate salt. For the particularly preferred redox initiator, it is preferred that the inorganic peroxodisulphate salt is potassium peroxodisulphate; and/or the aromatic amine is tert.-butyl-N,N-dimethylaniline (4-tert.-butyl-N,N-dimethylaniline); and/or the aromatic sulfinate salt is sodium para-toluenesulfinate. Most preferably, the redox initiator contains (i') potassium peroxodisulphate, (ii') 4-tert.-butyl-N,N-dimethylaniline, and (iii') sodium para-toluenesulfinate.

Preferably, a dual cure initiator system contains the photoinitiator system with the covalently bonded initiator compound X or Z having formula (XVI), (III) or (IV), and the redox initiator contains (i) an inorganic peroxodisulphate salt, (ii) an aromatic amine, and (iii) an aromatic sulfinate salt, more preferably the redox initiator contains (i') potassium peroxodisulphate, (ii') tert.-butyl-N,N-dimethylaniline, and (iii') sodium para-toluenesulfinate.

The above described initiator compounds may be linked to the initiator modified polyacidic polymer by a covalent bond. This linkage may be achieved analogously as described above for the process for preparing the photoinitiator modified polyacidic polymer having repeating units of formula (I), that is by reacting a precursor polyacidic polymer having repeating units of formula (VI) provided by step (a) in a subsequent step (b) with derivatives of the any one of the above described photoinitiators/sensitizers, electron donors and coinitiators, which derivatives have a reactive group capable of reacting with the COOH groups of the precursor polyacidic polymer having repeating units of formula (VI). Preferably, these derivatives have a reactive group selected from an isocyanate group, an amine group, an alcohol group or a halogen atom selected from Cl, Br or I.

Water-Soluble, Hydrolysis-Stable Monomer (c)

Optionally, the dental resin-modified glass Ionomer composition according to the invention comprises (c) a water-soluble, hydrolysis-stable monomer having a single polymerizable double bond and optionally a carboxylic acid group or hydroxyl group, which monomer is termed as "monomer (c)" hereinafter. The dental resin-modified glass ionomer composition may comprise one or a mixture of two or more of monomers (c).

The term "polymerizable double bond" as used herein in connection with monomer (c) means any double bond capable of addition polymerization, in particular free radical polymerization, preferably a carbon-carbon double bond.

The term "hydrolysis-stable" used in this connection means that the monomer (c) is stable to hydrolysis in an acidic medium, such as in a dental composition. In particular, the monomer (c) does not contain groups, e.g. as ester groups, which hydrolyse in aqueous media at pH 3 at room temperature within one month.

Further, the term "water-soluble" used in this connection means that at least 0.1 g, preferably 0.5 g of the monomer (c) dissolves in 100 g of water at 20° C.

The optional hydrolysis-stable, water-soluble monomer (c) may provide for a further improvement of the mechanical characteristics of the present dental resin-modified glass ionomer composition in cured form. Because, monomer (c) may for example polymerize together with a crosslinker having at least two polymerizable carbon-carbon double-bonds, whereby a crosslinked polymer network is formed.

Monomer (c) is hydrolysis stable, that is it preferably does not contain groups hydrolysing at pH 3 within one month. In particular, a suitable monomer (c) does not contain any ester group.

Furthermore, monomer (c) contains has a single double bond. Suitable polymerizable double bonds are carbon-carbon double bonds such as alkenyl groups and vinyl groups.

Preferably, monomer (c) has a carboxylic acid group and is a compound represented by the general formula (XX):

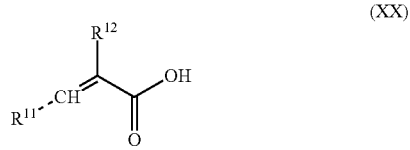

(XX)

In formula (XX), $R^{11}$ is a hydrogen atom or a straight chain or branched $C_{1-3}$ alkyl group, and $R^{12}$ is a hydrogen atom or a straight-chain or branched $C_{1-6}$ alkyl group which may be substituted by a —COOH group. In formula (XX), the dotted line indicates that $R^{11}$ may be in either the cis or trans orientation. Preferably, $R^{11}$ is a hydrogen atom, and $R^{12}$ is a hydrogen atom or a $C_{1-3}$ alkyl group optionally substituted with a —COOH group. More preferably, $R^{11}$ is a hydrogen atom, and $R^{12}$ is a hydrogen atom or a methyl group substituted with a —COOH group, that is compound of formula (XX) is acrylic acid or itaconic acid. Most preferably, the compound of formula (XX) is acrylic acid.

It is preferred that in formula (XX), residues $R^{11}$ and $R^{12}$ are selected with the proviso that the molecular weight of the monomer having a single polymerizable double bond according to (D) is at most 200 Da, preferably at most 150 Da, more preferably at most 100 Da.

Furthermore, monomer (c) may be 2-hydroxyethyl acrylamide (HEAA), N,N-dimethyl(meth)acrylamide, N,N-diethyl(meth)acrylamide, N,N-di-n-propyl(meth)acrylamide, and N-ethyl-N-methyl(meth)acrylamide.

Monomer (c) is preferably selected in view of a good processability and applicability of the final dental resin-modified glass ionomer composition, in particular in terms of viscosity. Therefore, the viscosity of monomer (c) is preferably in the range of 0.1 to 100 mPa·s, more preferably 0.3 to 50 mPa·s, even more preferably 0.5 to 25 mPa·s, yet even more preferably 0.8 to 10 mPa·s, in particular 0.9 to 3 mPa s.

Monomers (c) comprising a carboxylic acid group are particularly advantageous, since such monomers introduce additional carboxylic acid groups into a dental resin-modified glass ionomer composition. These additional carboxylic acid groups can undergo a cement reaction resulting in a further improved setting or curing reaction in the presence of a reactive particulate filler (a).

Preferably, monomer (c) is contained in the dental resin-modified glass ionomer composition in an amount of from 0.1 to 20, more preferably 1 to 15 even more preferably 2 to 10 percent by weight based on the total weight of the dental resin-modified glass ionomer composition. When monomer (c) is absent, a long-term mechanical resistance may be low. On the other hand, when the amount of monomer (c) exceeds 20 percent of weight, shrinkage of the dental glass ionomer cement obtained from the dental resin-modified glass ionomer composition may occur.

Water-Soluble, Hydrolysis-Stable Polymerizable Crosslinker (d)

Optionally, the dental resin-modified glass ionomer composition according to the invention comprises (d) a water-soluble, hydrolysis-stable polymerizable crosslinker having at least two polymerizable carbon-carbon double bonds, which crosslinker is termed as "crosslinker (d)" hereinafter. The dental resin-modified glass ionomer composition may comprise one or a mixture of two or more crosslinkers (d).

The term "polymerizable carbon-carbon double bond" as used herein in connection with crosslinker (d) means any carbon-carbon double bond capable of addition polymerization, in particular free radical polymerization.

Crosslinker (d) may be an alkylenediol dimethylacrylate such as 1,3-butanediol dimethacrylate, 1,4-butanediol dimethacrylate, an alkylenediol divinyl ether such as 1,4-butanediol divinyl ether, di(ethylene glycol) dimethacrylate, di(ethylene glycol) divinyl ether, pentaerythritol diacrylate monostearate, ethylene glycol dimethacrylate, trimetylolpropane trimethacrylate, pentaerythritol triacrylate or triallyl ether, pentaerythritol tetraacrylate and trimetylolpropane triacrylate.

Preferably, the crosslinker (d) is a polymerizable compound of the following formula (XXI), which is disclosed in EP2705827 and WO2014040729:

$$A\text{—}L^c(B)_{n'}$$

(XXI)

wherein

A is a group of the following formula (XXII)

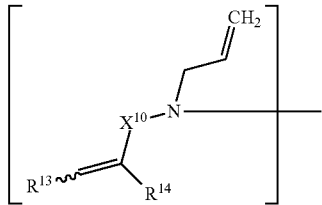

(XXII)

$X^{10}$ is CO, CS, $CH_2$, or a group $[X^{100}Z^{10}]_k$, wherein $X^{100}$ is an oxygen atom, a sulfur atom or NH, $Z^{10}$ is a straight chain or branched $C_{1-4}$ alkylene group, and k is an integer of from 1 to 10;

$R^{13}$ is a hydrogen atom,

—$COOM^{10}$, a straight chain or branched $C_{1-16}$ alkyl group which may be substituted by a $C_{3-6}$ cycloalkyl group, a $C_{6-14}$ aryl or $C_{3-14}$ heteroaryl group, —$COOM^{10}$, —$PO_3M^{10}$, —O—$PO_3M^{10}{}_2$ or —$SO_3M^{10}$, a $C_{3-6}$ cycloalkyl group which may be substituted by a $C_{1-16}$ alkyl group, a $C_{6-14}$ aryl or $C_{3-14}$ heteroaryl group, —$COOM^{10}$, —$PO_3M^{10}$, —O—$PO_3M^{10}{}_2$ or —$SO_3M^{10}$, a $C_{6-14}$ aryl or $C_{3-14}$ heteroaryl group which may be substituted by —$COOM^{10}$, —$PO_3M^{10}$, —O—$PO_3M^{10}{}_2$ or —$SO_3M^{10}$, $R^{14}$ is a hydrogen atom,

—$COOM^{10}$ a straight chain or branched $C_{1-16}$ alkyl group which may be substituted by a $C_{6-14}$ aryl or $C_{3-14}$ heteroaryl group, —$COOM^{10}$, —$PO_3M^{10}$, —O—$PO_3M^{10}$ and —$SO_3M^{10}$, a $C_{3-6}$ cycloalkyl group which may be substituted by a $C_{1-16}$ alkyl group, a $C_{6-14}$ aryl or $C_{3-14}$ heteroaryl group, —$COOM^{10}$, —$PO_3M^{10}$, —O—$PO_3M^{10}{}_2$ or —$SO_3M^{10}$, or a $C_{6-14}$ aryl or $C_{3-14}$ heteroaryl group which may be substituted by —$COOM^{10}$, —$PO_3M^{10}$, —O—$PO_3M^{10}{}_2$ and —$SO_3M^{10}$, $L^c$ is a single bond or a linker group;

B independently is a group according to the definition of A, a group of the following formula (XXIII)

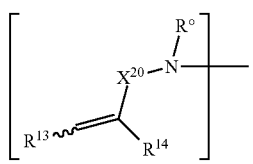

(XXIII)

wherein $X^{20}$ independently has the same meaning as defined for $X^1$ in formula (XXII), $R^{13}$ and $R^{14}$ are independent from each other and independently have the same meaning as defined for formula (XXII), $R^o$ is a hydrogen atom, a straight chain or branched $C_{1-16}$ alkyl group which may be substituted by a $C_{3-6}$ cycloalkyl group, a $C_{6-14}$ aryl or $C_{3-14}$ heteroaryl group, —$COOM^{10}$, —$PO_3M^{10}$, —O—$PO_3M^{10}{}_2$ or —$SO_3M^{10}$, a $C_{3-6}$ cycloalkyl group which may be substituted by a $C_{1-16}$ alkyl group, a $C_{6-14}$ aryl or $C_{3-14}$ heteroaryl group, —$COOM_{10}$, —$PO_3M^{10}$, —O—$PO_3M^{10}{}_2$ or —$SO_3M^{10}$, a $C_{6-14}$ aryl group which may be substituted by —$COOM^{10}$, —$PO_3M^{10}$, —O—$PO_3$ $M^{10}{}_2$ or —$SO_3M^{10}$, a group of the following formula (XXIV)

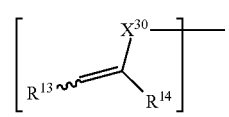

(XXIV)

wherein $X^{30}$ is CO, —$CH_2CO$—, CS, or —$CH_2CS$—, $R^{13}$ and $R^{14}$ which are independent from each other and independently have the same meaning as defined for formula (XXII), or a group $[X^{40}Z^{200}]_pE$, wherein $Z^{200}$ is a straight chain or branched $C_{1-4}$ alkylene group, $X^{40}$ is an oxygen atom, a sulfur atom or NH, E is a hydrogen atom, $PO_3M_2$, a straight chain or branched $C_{1-6}$ alkyl group which may be substituted by a $C_{3-6}$ cycloalkyl group, a $C_{6-14}$ aryl or $C_{3-14}$ heteroaryl group, —$COOM^{10}$, —$PO_3M_{10}$, —O—$PO_3M^{10}{}_2$ or —$SO_3M^{10}$, a $C_{3-6}$ cycloalkyl group which may be substituted by a $C_{1-6}$ alkyl group, a $C_{6-14}$ aryl or $C_{3-14}$ heteroaryl group, —$COOM^{10}$, —$PO_3M^{10}$, —O—$PO_3M^{10}{}_2$ or —$SO_3M^{10}$, a $C_{6-14}$ aryl or $C_{3-14}$ heteroaryl group which may be substituted by —$COOM^{10}$, —$PO_3M^{10}$, —O—$PO_3M^{10}{}_2$ or —$SO_3M^{10}$, and $p^c$ is an integer of from 1 to 10;

and n' is an integer of from 1 to 4;

wherein $M^{10}$ which are independent from each other each represent a hydrogen atom or a metal atom. Preferably, when $L^c$ is a single bond, B cannot be a group according to the definition of A or a group of the formula (XXIII).

The following groups are preferred groups of formula (XXII), wherein $M^{10}$ is a hydrogen atom or a metal atom:

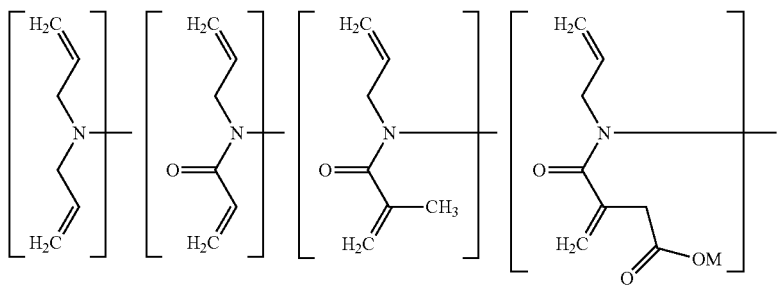

Preferred divalent linker groups may be selected from methylene, ethylene, propylene, butylene and the following divalent groups:

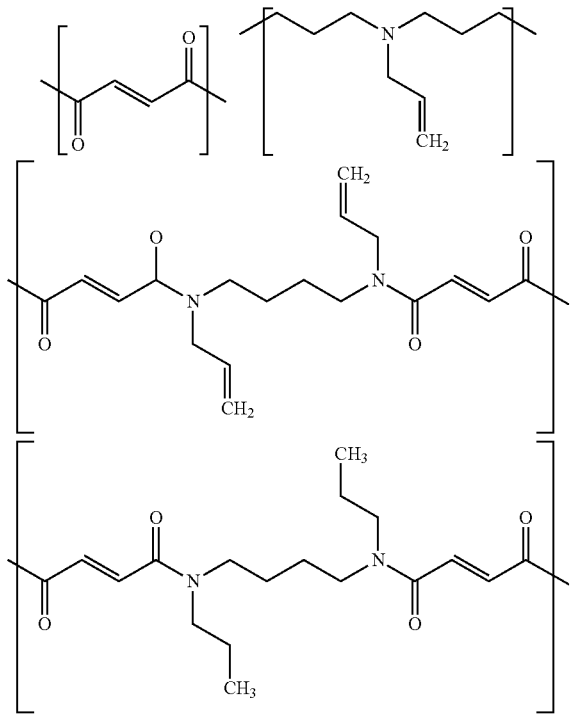

N,N''-(2E)-but-2-en-1,4-diallylbis-[(N-prop-2-en-1) amide and N,N-di(allylacrylamido) propane are preferred.

Further Optional Components

The dental resin-modified glass ionomer composition according to the present invention may, besides of optional components monomer (c) and/or crosslinker (d), comprise additional optional components.

The dental resin-modified glass ionomer composition according to the present invention may contain further components such as further fillers besides of reactive particulate filler (a), components improving radio-opacity, solvents, free radical scavengers such as 4-methoxyphenol, polymerization inhibitors, surfactants (such as to enhance solubility of an inhibitor e. g., polyoxyethylene), coupling agents to enhance reactivity of fillers e.g. 3-(trimethoxysilyl) propyl methacrylate, and rheology modifiers.

Further filler(s) besides of the reactive particulate filler (a) may for example be selected from inert glass(es), fluoride releasing glass(es), granulated prepolymerized fillers, ground prepolymerized fillers and filler aggregates.

The term "inert glass(es)" refers to a glass which is not capable of reacting with a polymer containing acidic groups in a cement reaction. Inert glasses are for example described in the Journal of Dental Research June 1979, pages 1607-1619, or more recently in U.S. Pat. Nos. 4,814,362, 5,318,929, 5,360,770, and application US 2004/0079258 A1. Specifically, from US 2004/0079258 A1, inert glasses are known in which strongly basic oxides such as CaO, BaO, SrO, MgO, ZnO, $Na_2O$, $K_2O$, $Li_2O$ etc. are replaced with weakly basic oxides such as those in the Scandium or Lanthanide series.

The term "fluoride releasing glass(es)" refers to a glass capable to of releasing fluoride. Fluoride releasing capability may be provided by adding to a mixture of oxides for forming a glass inorganic particles containing fluoride with the proviso that the glass has fluoride releasability, preferably sustained fluoride releasability. Such inorganic particles may be selected from the group consisting of sodium fluoride, strontium fluoride, lanthanum fluoride, ytterbium fluoride, yttrium fluoride, and calcium-containing fluoroaluminosilicate glasses.

The term "silanated" as used herein means that the filler has silane coupling agent(s) on its surface, for example in the form of a coating at least partly, and preferably fully covering the surface of the filler.

Components improving radio-opacity may for example be selected from $CaWO_4$, $ZrO_2$ and $YF_3$.

Suitable solvents may be selected from water, alcohols such as methanol, ethanol, propanol (n-, i-), butanol (n-, iso-, tert.-), and ketones such as acetone.

One-Pack or Multi-Pack Dental Composition

The present dental resin-modified glass ionomer composition may be a one-pack or a multi-pack dental composition.

The term "one-pack" as used herein means that all components of the dental resin-modified glass ionomer composition are comprised in one single pack such as a capsule having at least two chambers or a double barrel syringe.

The term "multi-pack" as used herein means that the components of the dental resin-modified glass ionomer composition are comprised in a multitude of separate packs. For example, a first part of components is comprised in a first pack, while as second part of components is comprised in a second pack, a third part of components may be comprised in a third pack, a fourth part of components may be comprised in a fourth pack, and so on.

Preferably, the dental resin-modified glass ionomer composition is a composition of two or more packs, more preferably a two-pack composition. For a two-pack dental composition, a two-pack powder/liquid composition is preferred.

Preferably, in a two-pack powder/liquid composition, the powder pack comprises (a) the reactive particulate filler, and the liquid pack comprises (b) the polyacidic polymer which is reactive with the reactive particulate filler in a cement reaction.

The Cured Dental Resin-Modified Glass Ionomer Composition

The present dental resin-modified glass ionomer composition is a curable dental composition. A cured dental glass ionomer composition/cement can be obtained therefrom by reacting the reactive particulate filler (a) with the polyacidic polymer (b) by means of cement reaction, wherein in addition, a photopolymerization is initiated by the photoinitiator system.

It was found that the cured present dental resin-modified glass ionomer composition according has the following particularly advantageous mechanical properties:

A flexural strength of at least 80 MPa as measured according to ISO 4049; and/or an adhesion to enamel and/or dentine is of at least 5 MPa as measured according to ISO 29022:2013.

Particularly Preferred Embodiment

According to a particularly preferred embodiment, the initiator modified polyacidic polymer has repeating units of formula (I'):

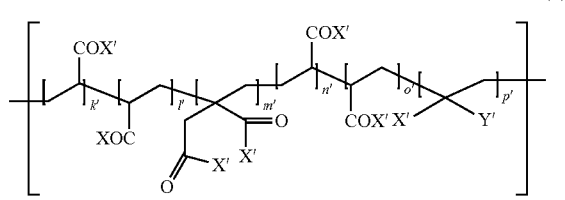

wherein

X', which may be the same or different, independently represent OH, or NH—L'—Z', wherein L' is a single bond or a divalent linker group having the following formula (V')

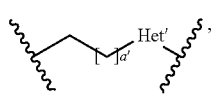

wherein a' is 0 or an integer of from 1 to 6, and

Het' is oxygen or NH, preferably a' is 0 or an integer of from 1 to 3, and Het' is NH, more preferably L' is a single bond, and Z' is a covalently bonded initiator compound of formula (II'):

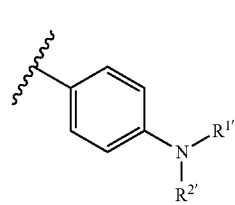

wherein

R[1'] and R[2']

which may be the same or different, independently represent a $C_{1-6}$ straight-chain, $C_{3-6}$ branched or cyclic alkyl group, preferably a $C_{1-4}$ straight-chain or branched alkyl group;

Y' is a hydrogen atom, COOH or a covalently bonded initiator compound;

k', l', m', n', o' and p' are independently integers of at least 0, k'+l'+m'+n'+o'+p' is at least 1, wherein it is preferred that m' and/or p' is 0, most preferably m and p' is 0; and at least one X' is present which is not OH when Y' is a hydrogen atom or COOH;

wherein the polyacidic polymer has a weight average molecular weight of 1 to 300 kDa.

Use of the Initiator-Modified Polyacidic Polymer Having Repeating Units of Formula (XV)

The initiator-modified polyacidic polymer having repeating units of formula (XV) as described above may be used for the preparation of a dental composition, preferably for the preparation of a dental resin-modified glass ionomer composition, most preferably for the preparation of the above described dental resin-modified glass ionomer composition.

The invention will now be further illustrated by the following Examples.

EXAMPLES

Example 1

Synthesis of Poly[(N-(4-(Dimethylamino Phenyl)Acrylamide)-Co-(Acrylic Acid)]

To a solution of 5 g polyacrylic acid (Mw 136.00 g/mol) in 15 ml dioxane at 40° C. were added 563 mg (69 mmol) 4-dimethylamino phenylisocyanat dissolved in 5 ml dioxane within 5 min. The solution was stirred overnight at 40° C. The reaction mixture cooled to room temperature was dropped into 200 ml acetonitrile. Then, the precipitated modified polymer was separated by decanting the overlaying solution, and dissolved in 100 ml water. The acetonitrile was removed by distillation at 100 mbar and 40° C. Then, the remaining solution was dialysed (MWCO=1000 Da), and the water was removed by freeze-drying.

Yield: 1.89 (36%)

Polymer modification ($^1$H NMR): appr. 2.5%

$^1$H NMR (DMSO-$d_6$): δ (ppm)=12.23 (s, COOH), 7.27-6.67 (m, Ar), 2.84-2.82 (d, CH$\underline{CH_2}$CH), 2.11 (s, CH), 1.51-1.33 (m, CH$_2\underline{CH_2}$CH),

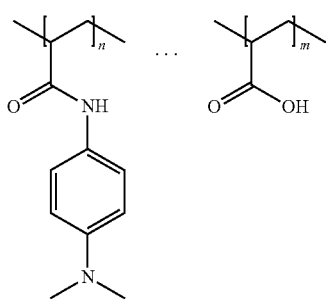

Application Examples 1 and 2 and Comparative Example 1

Aqueous dental glass ionomer compositions of Application Example 1 according to the invention and of the Comparative Example 1 have been prepared by forming a liquid and a powder composition of the ingredients listed in Table 1 below, which respectively add up to 100 wt %, and admixing both parts in the shown powder/liquid (P/L) ratio.

[Curing Time]

Working time: Period of time, measured from the start of mixing the powder and glass in the shown P/L ratio, during which it is possible to manipulate the material without an adverse effect on the properties.

Setting time: Point of time at which the mixture stopped being deformed even under pressing.

[Flexural Strength]

The obtained dental glass ionomer compositions of Example 1 and Comparative Example 1 were filled in a stainless steel mould having the size (25±2) mm×(2.0±0.1) mm×(2.0±0.1) mm, for the preparation of test specimens. The thus obtained dental glass ionomer compositions were cured with a dental curing light (light-cured, LC) as well as without external power source (self-cured, SC). For the resulting cured dental glass ionomer composition, the flexural strength has been determined according to ISO 4049.

TABLE 1

Composition and properties of Application example 1 and Comparative example 1

| | | Application Example 1 SAH 1-173-03A/ SAH 1-173-03B | Comparative Example 1 SAH 1-176-01A/ SKA 17-072-01 B |
|---|---|---|---|
| Liquid | Water | 33.8 | 33.8 |
| | Cross-linker | 15.0 | 15.0 |
| | Acrylic acid | 25.0 | 25.0 |
| | Modified polyacid | 20.0 | 25.0 |
| | Amine modified Polyacid of synthesis example 1 | 5.5 | — |
| | Camphorquinone + Inhibitor | 0.7 | 0.7 |
| | DMABN | — | 0.5 |
| | Σ | 100 | 100 |
| Powder | Reactive glass mixture | 99.34 | 99.34 |
| | KPS | 0.22 | 0.22 |
| | NapTS | 0.44 | 0.44 |
| | Σ | 100 | 100 |
| P/L ratio | | 3.0 | 3.0 (SC) 3.2 (LC) |
| Curing time | Working time (seconds) | 140 | 145 |
| | Setting time (seconds) | 277 | 285 |
| Flexural strength (SC) [MPa] | | 95 ± 17 | 84 ± 7 |
| E-Modulus (SC) [MPa] | | 12060 ± 910 | 10520 ± 340 |
| Flexural strength (LC) [MPa] | | 115 ± 5 | 117 ± 14 |
| E-Modulus (LC) [MPa] | | 12090 ± 410 | 12650 ± 370 |

| | | Example 2 (Amine Modified PAA Charge JBR 03-129-01) Liquid FSZ 01-145-01 Powder FSZ 01-143-01 |
|---|---|---|
| Liquid | Water | 33.85 |
| | Cross-linker | 15.0 |
| | Modified polyacid | 20.0 |
| | Amine Modified polyacid | 5.5 |
| | Acrylic acid | 25.0 |
| | DMAPAA | 0 |
| | CQ | 0.62 |
| | Inhibtitor | 0.03 |
| | Σ | 100 |
| Powder | Reactive glass mixture | 99.54 |
| | NapTS | 0.58 |
| | KPS | 0.88 |
| | Σ | 100 |
| P/L ratio | | 3.0 |

TABLE 1-continued

| Composition and properties of Application example 1 and Comparative example 1 | | | |
|---|---|---|---|
| Curing time | Working time (seconds) | 140 | SKA 17-121-01 A |
| | Setting time (seconds) | 200 | SKA 17-121-01 B |
| Flexural strength (SC) [MPa] | | 85 ± 12 | SKA 17-119-01 B |
| Flexural strength (LC) [MPa] | | 98 ± 3 | SKA 17-119-01 A |
| E-Modulus (SC) [MPa] | | 11000 ± 460 | SKA 17-119-01 B |
| E-Modulus (LC) [MPa] | | 12000 ± 500 | SKA 17-119-01 A |

The invention claimed is:

1. A dental resin-modified glass ionomer composition comprising
   (a) a reactive particulate filler, and
   (b) a polyacidic polymer which is reactive with the reactive particulate filler in a cement reaction,
   wherein the composition further comprises an initiator system consisting of one or more initiator compounds generating alone or in combination free radicals, wherein at least one of the one or more initiator compounds is linked to the polyacidic polymer (b) by a covalent bond forming an initiator modified polyacidic polymer having a covalently bonded initiator compound,
   wherein the initiator modified polyacidic polymer is a compound having repeating units of a following formula (I):

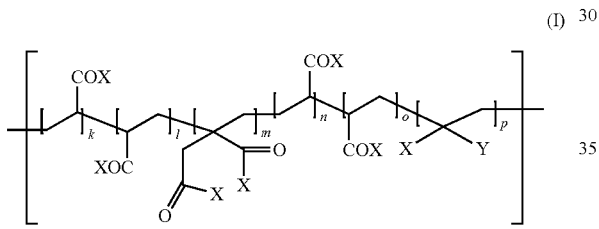

wherein
   X, which may be a same or different, and independently represent OH, O—L—Z, or NH—L—Z, wherein L is a single bond or a divalent linker group, and Z is a covalently bonded initiator compound;
   Y is a hydrogen atom, COOH or a covalently bonded initiator compound;
   wherein the covalently bonded initiator compound is selected from the group of benzophenone, 1,2-diketones, 1,3 diketones, aromatic amines, and phosphines;
   k, l, m, n, o and p are independently integers of at least 0,
   k+l+m+n+o+p is at least 1; and
   at least one X is present which is not OH when Y is a hydrogen atom or COOH;
   wherein the polyacidic polymer has a weight average molecular weight of 1 to 300 kDa;
   wherein the initiator modified polyacidic polymer contains 0.01 to 20 mole % covalently bonded initiator compound per 100 mole % of acidic groups of the polyacidic polymer.

2. The dental resin-modified glass ionomer composition according to claim 1, wherein the initiator system is a photoinitiator system consisting of one or more initiator compounds generating alone or in combination free radicals when irradiated with light having a wavelength in a range of from 400 to 800 nm.

3. The dental resin-modified glass ionomer composition according to claim 1, wherein the polyacidic polymer (b) is a polyacrylic acid or a copolymer of acrylic acid and itaconic acid.

4. The dental resin-modified glass ionomer composition according to claim 2, wherein the one or more initiator compounded is at least a Norrish type II photoinitiator comprising a sensitizer component and an electron donor component.

5. The dental resin-modified glass ionomer composition according to claim 1, wherein the covalently bonded initiator compound Y and Z are independent from each other and represent moieties of a following formula (II):

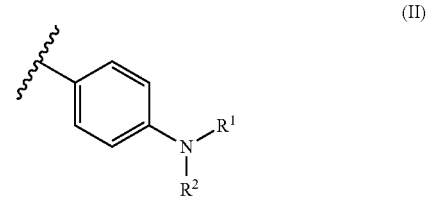

wherein
   $R^1$ and $R^2$ which may be a same or different, and independently represent a $C_{1-6}$ straight chain alkyl group, $C_{3-6}$ branched alkyl group or cyclic alkyl group.

6. The dental resin-modified glass ionomer composition according to claim 1, wherein a temporary or final restoration of a hard dental tissue is comprised of the dental resin-modified glass ionomer composition.

7. The dental resin-modified glass ionomer composition according to claim 1, which further comprises
   (c) a water-soluble, hydrolysis-stable monomer having a single polymerizable double bond and optionally a carboxylic acid group or hydroxyl group; and/or
   (d) a water-soluble, hydrolysis-stable polymerizable crosslinker having at least two polymerizable carbon-carbon double bonds.

8. The dental resin-modified glass ionomer composition according to claim 1, wherein the initiator modified polyacidic polymer contains 0.05 to 10 mole % covalently bonded initiator compound per 100 mole % of acidic groups of the initiator modified polyacidic polymer.

9. An initiator modified polyacidic polymer having a covalently bonded initiator compound, wherein the initiator modified polyacidic polymer contains 0.01 to 20 mole% covalently bonded initiator compound per 100 mole % of acidic groups of the initiator modified polyacidic polymer, wherein the initiator modified polyacidic polymer is a compound having repeating units of a following formula (I):

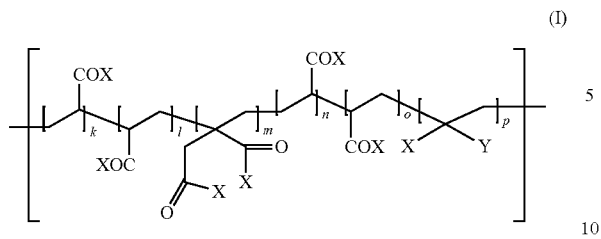
(I)

wherein
X, which may be a same or different, and independently represent OH, O—L—Z, or NH—L—Z,
wherein
L is a single bond or a divalent linker group, and
Z is a covalently bonded initiator compound;
Y is a hydrogen atom, COOH or a covalently bonded initiator compound;
wherein the covalently bonded initiator compound is selected from the group of benzophenone, 1,2-diketones, 1,3 diketones, aromatic amines, and phosphines;
k, l, m, n, o and p are independently integers of at least 0, k+l+m+n+o+p is at least 1; and
at least one X is present which is not OH when Y is a hydrogen atom or COOH;
wherein the polyacidic polymer has a weight average molecular weight of 1 to 300 kDa.

10. An initiator modified polyacidic polymer according to claim 9, wherein the covalently bonded initiator compound Y and Z are independent from each other, and represent moieties of a following formula (II):

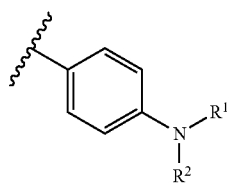
(II)

wherein
$R^1$ and $R^2$ which may be a same or different, and independently represent a $C_{1-6}$ straight chain alkyl group, $C_{3-6}$ branched alkyl group or cyclic alkyl group.

11. A method of forming a dental composition; said method comprising: mixing a composition comprising an initiator modified polyacidic polymer having a covalently bonded initiator compound with a reactive particulate filler to form the dental composition;
wherein the initiator modified polyacidic polymer is a compound having repeating units of a following formula (I):

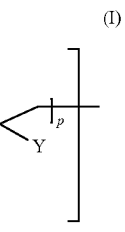
(I)

wherein
X, which may be a same or different, and independently represent OH, O—L—Z, or NH—L—Z,
wherein
L is a single bond or a divalent linker group, and
Z is a covalently bonded initiator compound;
Y is a hydrogen atom, COOH or a covalently bonded initiator compound;
wherein the covalently bonded initiator compound is selected from the group of benzophenone, 1,2-diketones, 1,3 diketones, aromatic amines, and phosphines;
k, l, m, n, o and p are independently integers of at least 0, k+l+m+n+o+p is at least 1; and
at least one X is present which is not OH when Y is a hydrogen atom or COOH;
wherein the polyacidic polymer has a weight average molecular weight of 1 to 300 kDa;
wherein the initiator modified polyacidic polymer contains 0.01 to 20 mole % covalently bonded initiator compound per 100 mole % of acidic groups of the polyacidic polymer.

12. The method according to claim 11, wherein the covalently bonded initiator compound Y and Z are independent from each other, and represent moieties of a following formula (II):

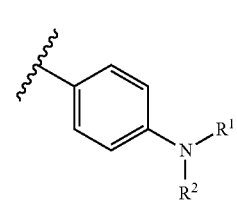
(II)

wherein
$R^1$ and $R^2$ which may be a same or different, and independently represent a $C_{1-6}$ straight chain alkyl group, $C_{3-6}$ branched alkyl group or cyclic alkyl group.

13. The dental resin-modified glass ionomer composition according to claim 1, wherein a luting cement for crown and bridge cementation is comprised of the dental resin-modified glass ionomer composition.

* * * * *